(12) United States Patent
Glinka

(10) Patent No.: US 6,599,893 B2
(45) Date of Patent: Jul. 29, 2003

(54) CEPHALOSPORIN ANTIBIOTICS AND PRODRUGS THEREOF

(75) Inventor: Tomasz W. Glinka, Cupertino, CA (US)

(73) Assignee: Essential Therapeutics, Inc., Mountain View, CA (US)

(*) Notice: Subject to any disclaimer, the term of this patent is extended or adjusted under 35 U.S.C. 154(b) by 0 days.

(21) Appl. No.: 09/925,217

(22) Filed: Aug. 8, 2001

(65) Prior Publication Data

US 2002/0115650 A1 Aug. 22, 2002

Related U.S. Application Data

(60) Provisional application No. 60/229,174, filed on Aug. 29, 2000.

(51) Int. Cl.[7] .................... C07D 501/59; A61K 31/546; A61D 31/04

(52) U.S. Cl. .................... 514/206; 514/204; 544/226; 544/227

(58) Field of Search ................. 514/204, 206; 540/226, 227

(56) References Cited

U.S. PATENT DOCUMENTS 6,030,965 A * 2/2000 Cho et al. .................... 540/227

FOREIGN PATENT DOCUMENTS

| EP | 9008 | * | 3/1980 | |
|----|------|---|--------|---|
| JP | 09278778 A | * | 10/1997 | ......... A61K/31/545 |

* cited by examiner

Primary Examiner—Mark L. Berch
(74) Attorney, Agent, or Firm—Bernard F. Rose; Bingham McCutchen LLP

(57) ABSTRACT

The present invention relates to chemical compounds having the formula:

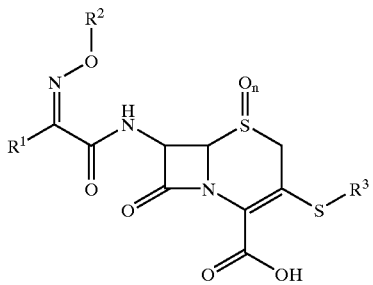

or a pharmaceutically acceptable salt thereof. $R^1$ is selected from the group consisting of:

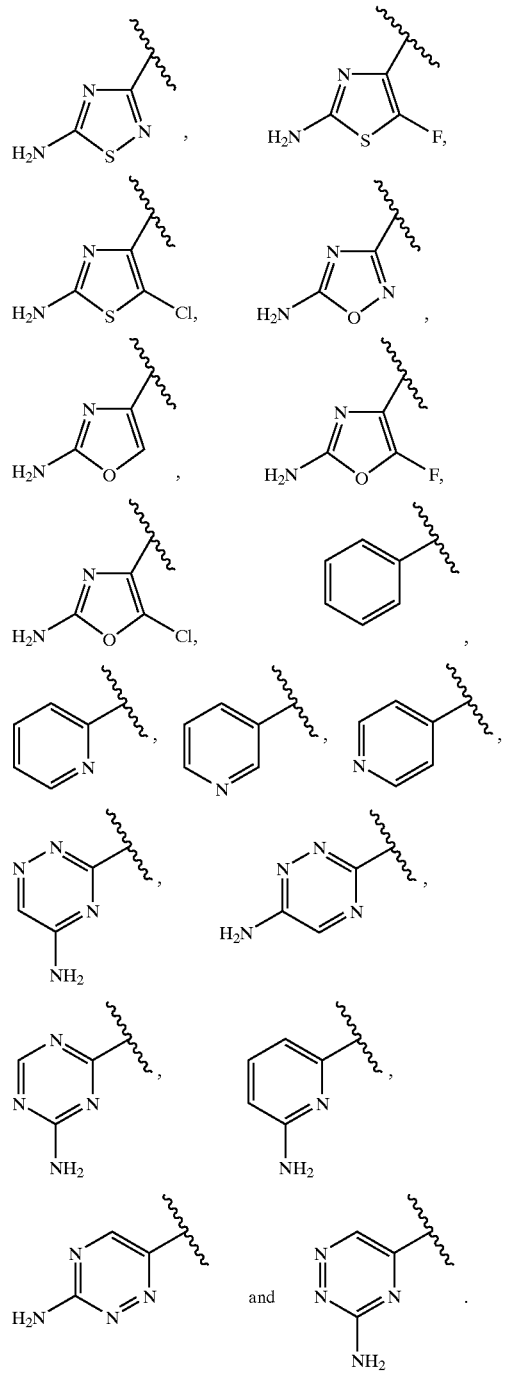

$R^2$ is selected from the group consisting of hydrogen, $CH_3-$, $FCH_2-$, $F_2CH-$

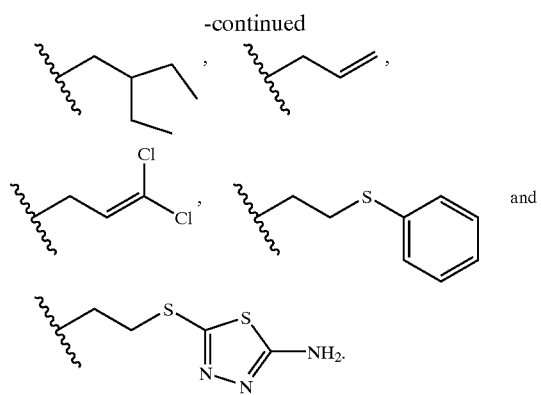
$R^3$ is selected from the group consisting of:
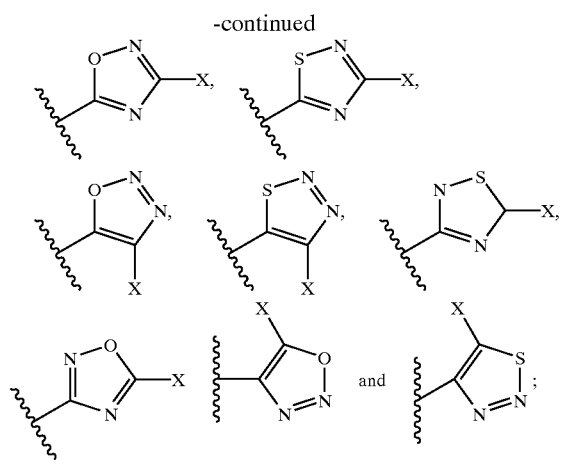
X is selected from the group consisting of hydrogen, halogen, cyano, —$NH_2$, —$N(CH_3)_2$, —$HSO_2NH_2$, —$SO_2NH_2$ and —$SCH_3$. The subscript n is 0 or 1.
12 Claims, No Drawings

CEPHALOSPORIN ANTIBIOTICS AND PRODRUGS THEREOF

RELATED APPLICATIONS

This application is related to and claims priority from Provisional Patent Application Serial No. 60/229,174, filed Aug. 29, 2000, which is incorporated by reference as if fully set forth herein.

FIELD OF THE INVENTION

The present invention relates to novel cephalosporin antibiotics and prodrugs thereof. It also relates to methods for the synthesis of the compounds and for their use against a broad spectrum of bacteria, including many that are resistant to conventional beta-lactam antibiotics.

BACKGROUND OF THE INVENTION

The following is provided to aid in the understanding of the present invention. Nothing in this section is to be construed as prior art to the present invention.

Over the past three decades a variety of antibiotics have become available for clinical use. One class of antibiotics that has seen remarkable growth is the cephalosporins, over 70 of which have entered clinical use since 1965.

Unfortunately, the widespread use of antibiotics has resulted in an alarming increase in the number of resistant bacterial strains, especially among clinically important bacterial such as those of the genera Staphylococcus, Salmonella, Enterobacteriaceœ and Pseudomonas, in particular, the species *S. aureus* and *S. pneumoniœ*.

Bacterial resistance to cephalosporins arises primarily by (a) destruction of the antibiotic by β-lactamases; (b) decreased penetration due to changes in bacterial outer membrane composition; and (c) interference with β-lactam binding to penicillin-binding proteins (PBPs). The last mechanism is especially important because the binding of β-lactams to PBPs is an essential step in the inhibition of glycoprotein biosynthesis by this class of antibiotics (glycoprotein being a required bacterial cell-wall component).

Certain gram-positive bacteria are highly resistant to beta-lactam antibiotics such as methicillin-resistant *Staphylococcus aureus* (MRSA) and various enterococci species. The resistance of MRSA is due to the presence of a PBP known as PBP2a, which binds very poorly to β-lactam antibiotics. Currently, to overcome this resistance, the glycopeptides vancomycin and teicoplanin, which are not dependent on PBP-binding are the antibiotics of choice for treatment of MRSA-induced bacteremia. The quinolone antibacterials and some carbapenems, such as imipenem, also have been reported to be active against a few MRSA strains, but their use is being rapidly limited by the emergence of resistant MRSA strains.

Recent advances in compounds, compositions and methods for treating infections caused by β-lactam antibiotic resistant bacteria are described in commonly owned International Application No. PCT/US95/03976 and U.S. patent applications Ser. Nos. 08/222,262, filed Apr. 1, 1994; 08/369,798, filed Jan. 6, 1995; 08/413,713, 08/413,714, 08/415,065, 08/413,712, 08/415,064, and 08/415,069, all of which were filed on Mar. 29, 1995; 08/455,969, filed May 31, 1995; 08/457,673, filed Jun. 1, 1995; 08/940,508 and 08/937,812, both of which were filed Sep. 29, 1997; 08/730,041, 08/730,039, 08/728,232, 08/430,042, 08/728,233, and 08/730,040, all of which were filed Oct. 11, 1996; and 08/842,915, filed Apr. 17, 1997 and 60/155,496, filed Sep. 22, 1999; all of which are incorporated by reference herein, including any drawings. In addition, International Application No. PCT/WO95/07283, filed Sept. 8, 1994, describes new cephem compounds, and is likewise incorporated by reference herein.

Despite the advances being made in the battle against β-lactam resistant bacteria, there remains a need for newer and better antibiotics to combat the ever-increasing incidence of resistance. The present invention provides such compounds.

SUMMARY OF THE INVENTION

The present invention relates to compounds, compositions and methods for treating infections in mammals arising from beta-lactam antibiotic resistant bacteria. Preferred compounds will have a minimum inhibitory concentration (MIC) that is less than the MIC of cefotaxime or imipenem against a beta-lactam resistant organism, in particular a methicillin-resistant Staphylococcal organism. Of course, the compounds of this invention will also be an effective alternative to conventional beta-lactam antibiotics against organisms that are still susceptible to the conventional compounds.

Thus, in one aspect, the present invention relates to a compound, or a pharmaceutically acceptable salt thereof, having the chemical structure

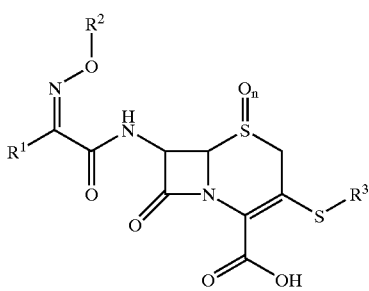

wherein $R^1$ is selected from the group consisting of

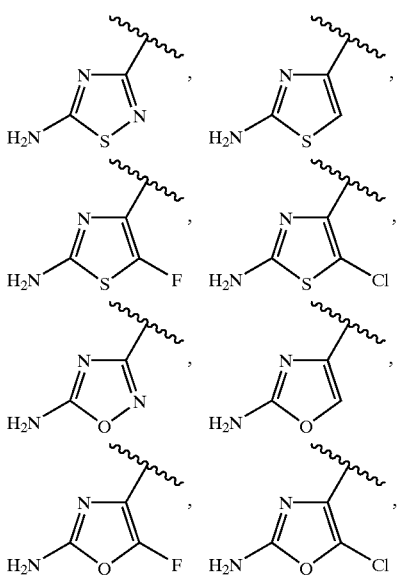

-continued

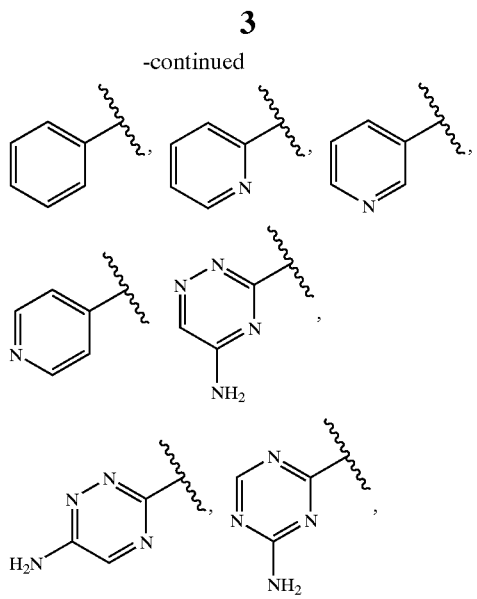

$R^2$ is selected from the group consisting of hydrogen, $CH_3$—, $FCH_2$—, $F_2CH$—,

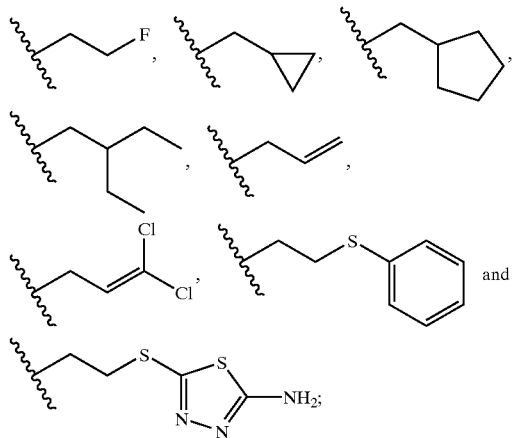

$R^3$ is selected from the group consisting of

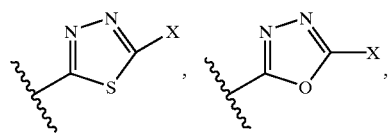

-continued

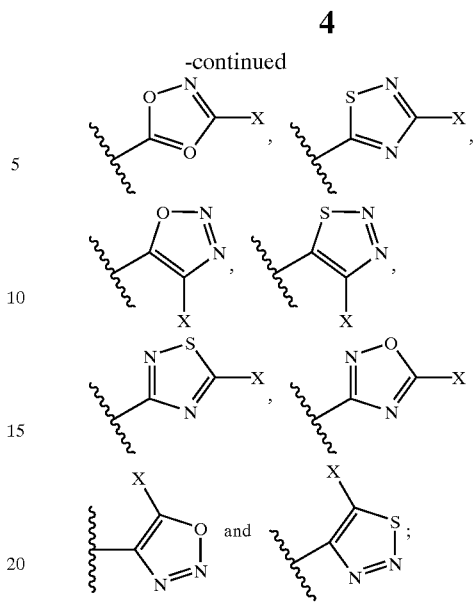

wherein X is selected from the group consisting of hydrogen, halogen, cyano, —$NH_2$, —$N(CH_3)_2$, —$NHSO_2NH_2$, —$SO_2NH_2$ and —$SCH_3$; and, n is 0 or 1.

An aspect of this invention is compound 1, wherein $R^1$ is selected from the group consisting of

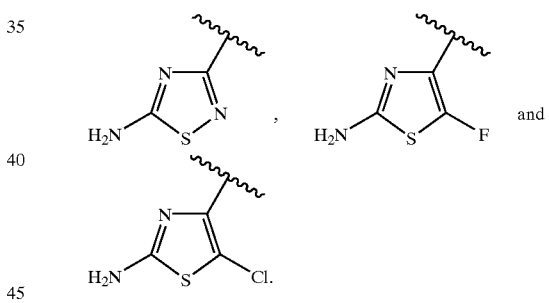

An aspect of this invention is compound 1, wherein $R^2$ is selected from the group consisting of hydrogen, and

An aspect of this invention is compound 1, wherein $R^3$ is selected from the group consisting of

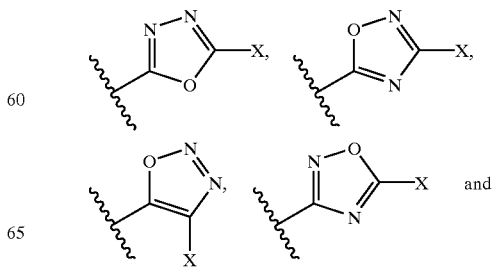

-continued

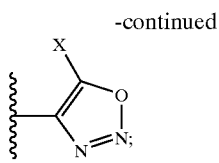

wherein X is selected from the group consisting of hydrogen, halogen, cyano, —NH$_2$, —N(CH$_3$)$_2$, —NHSO$_2$NH$_2$, —SO$_2$NH$_2$ and —SCH$_3$.

An aspect of this invention is compound 1, wherein R$^1$ is selected from the group consisting of

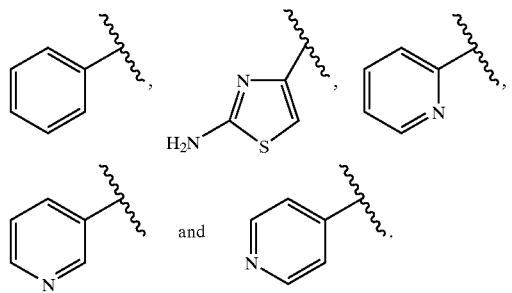

An aspect of this invention is compound 1, wherein R$^1$ is selected from the group consisting of

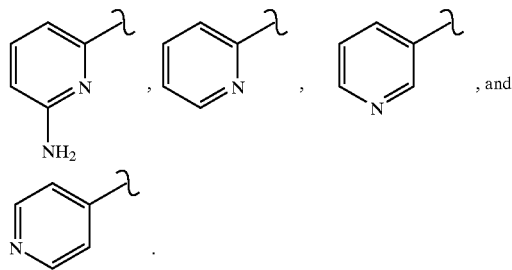

An aspect of this invention is compound 1, wherein R$^2$ is selected from the group consisting of CH$_3$—, FCH$_2$—, F$_2$CH—,

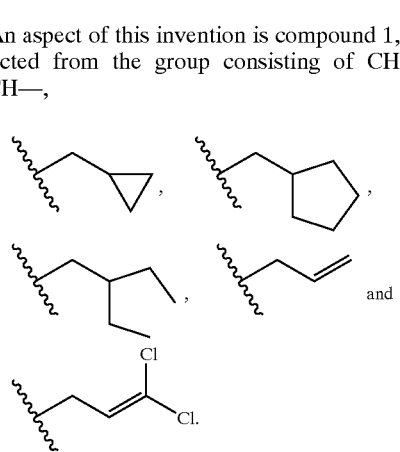

An aspect of this invention is compound 1, wherein R$^2$ is selected from the group consisting of

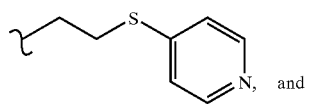

-continued

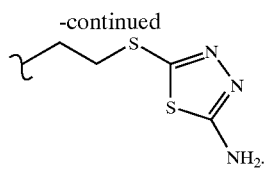

An aspect of this invention is compound 1, wherein R$^3$ is selected from the group consisting of

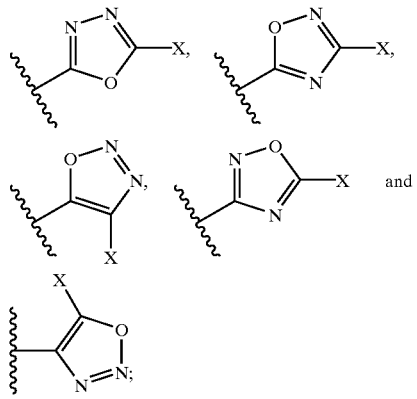

wherein X is selected from the group consisting of hydrogen, halogen, cyano, —NH$_2$, —N(CH$_3$)$_2$, —NHSO$_2$NH$_2$, —SO$_2$NH$_2$ and —SCH$_3$.

In the above compound, X is —NH$_2$ in another aspect of this invention.

An aspect of this invention is compound 1, wherein R$^1$ is selected from the group consisting of

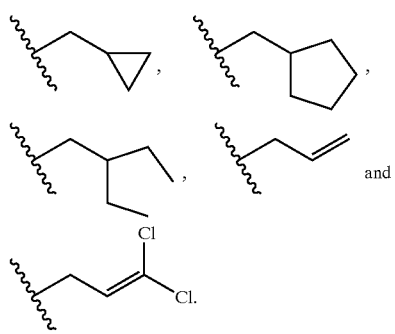

An aspect of this invention is compound 1, wherein R$^2$ is selected from the group consisting of:

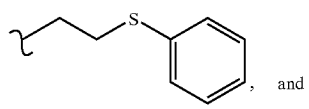

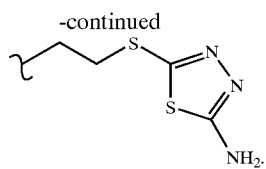

An aspect of this invention is compound 1, wherein

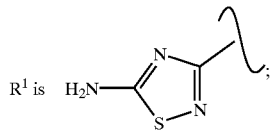

$R^2$ is hydrogen; and

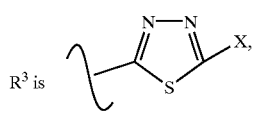

wherein X is —$NH_2$.

An aspect of this invention is a compound having structure 1 wherein

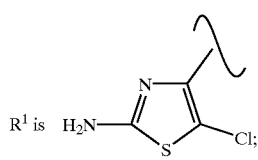

$R^2$ is hydrogen; and

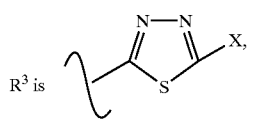

wherein X is —$NH_2$.

An aspect of this invention is a compound having structure 1 wherein the compound is active against methicillin-resistant Staphylococci, as demonstrated by a lower minimum inhibitory concentration than methicillin against *S. aureus* Col (Meth$^R$)(bla−), *S. aureus* 76 (Meth$^R$)(bla+), *S. aureus* ATCC 33593 (Meth$^R$), *S. aureus* Spain #356 (Meth$^R$), and/or *S. haemolyticus* 05 (Meth$^R$).

An aspect of this invention is a method for treating a methicillin-resistant Staphylococcal infection comprising administering to a patient in need thereof a therapeutically effective amount of a compound having structure 1.

An aspect of this invention is an antibacterial composition comprising a therapeutically effective amount of a compound having structure 1 together with a pharmaceutically acceptable carrier.

An aspect of this invention is the use of the above composition for the treatment of a methicillin-resistant Staphylococcal infection.

An aspect of this invention is a prodrug, or pharmaceutically acceptable salt thereof, having chemical structure 2:

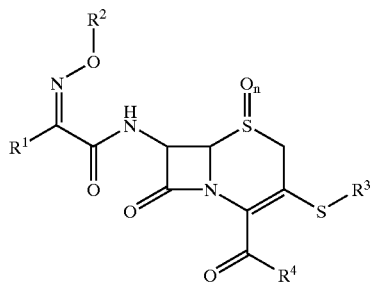

wherein $R^1$ is selected from the group consisting of

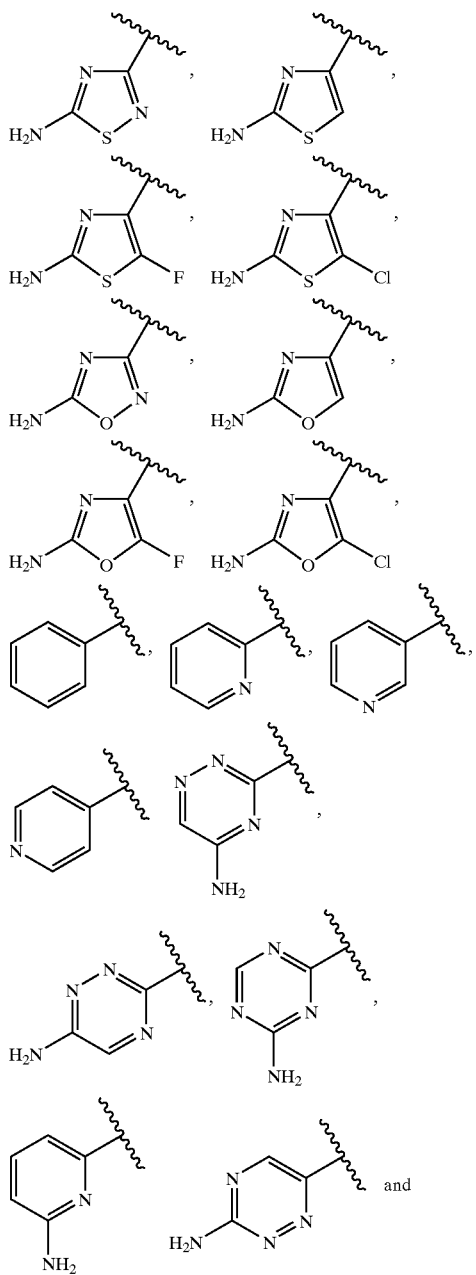

and

-continued

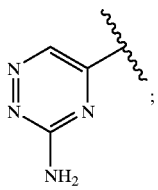

R² is selected from the group consisting of hydrogen, CH₃—, FCH₂—, F₂CH—,

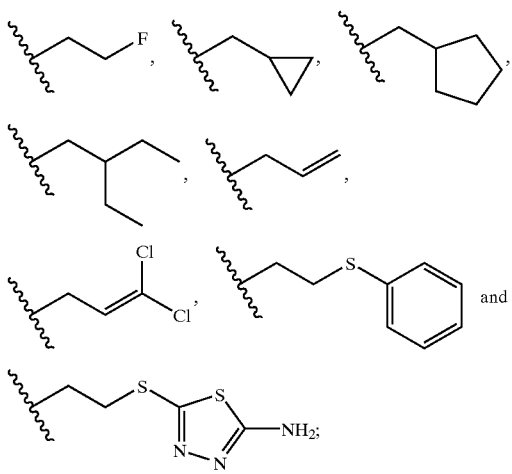

and

R³ is selected from the group consisting of

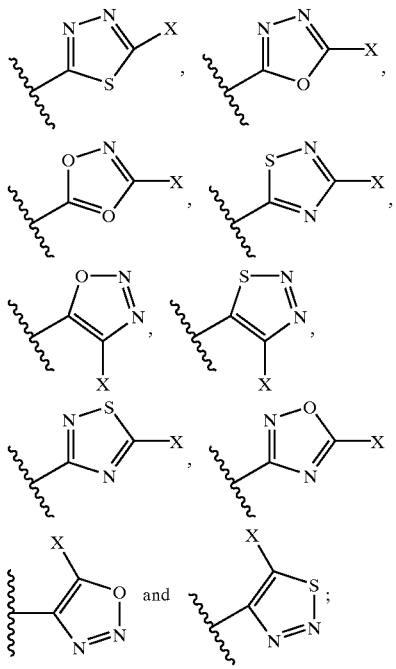

wherein X is selected from the group consisting of hydrogen, halogen, cyano, —NH₂, —N(CH₃)₂, —NHSO₂NH₂, —SO₂NH₂ and —SCH₃;

R⁴ is selected from the group consisting of

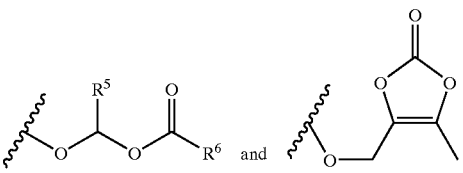

R⁵ is selected from the group consisting of hydrogen and CH₃—;

R⁶ is selected from the group consisting of CH₃—, CH₃CH₂—, CH₃CH₂CH₂—, CH₃CH(CH₃)—, (CH₃)₃C—, CH₃O—, CH₃CH₂O—, CH₃CH₂CH₂O—, CH₃CH(CH₃)O— and (CH₃)₃CO—; and, n is 0 or 1.

An aspect of this invention is prodrug 2, wherein R¹ is selected from the group consisting of

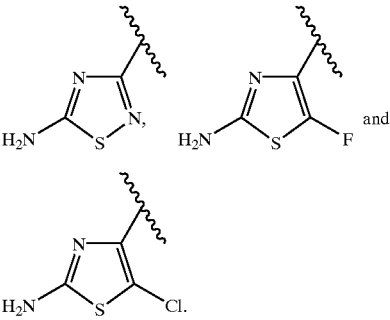

An aspect of this invention is prodrug 2, wherein R² is selected from the group consisting of
hydrogen, and

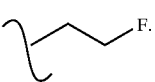

An aspect of this invention is prodrug 2 wherein R³ is selected from the group consisting of

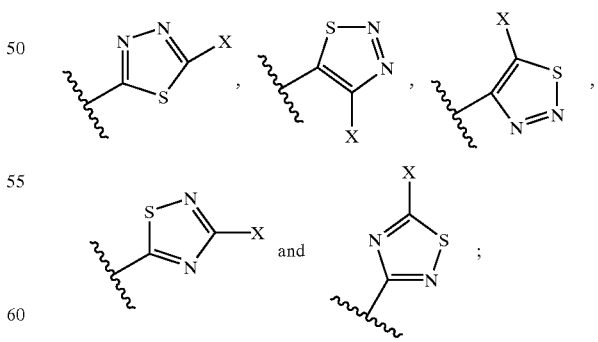

wherein X is selected from the group consisting of hydrogen, halogen, cyano, —NH₂, —N(CH₃)₂, —NHSO₂NH₂, —SO₂NH₂ and —SCH₃.

An aspect of this invention is prodrug 2, wherein $R^1$ is selected from the group consisting of

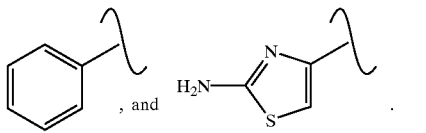

An aspect of this invention is prodrug 2, wherein $R^1$ is selected from the group consisting of

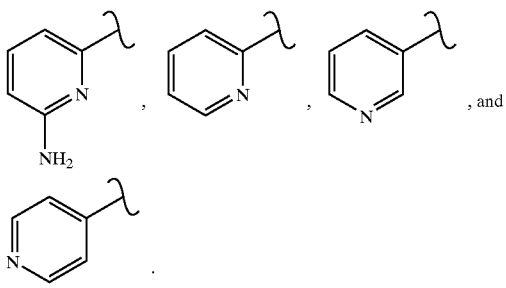

An aspect of this invention is prodrug 2, wherein $R^2$ is selected from the group consisting of $CH_3$—, $FCH_2$—, $F_2CH$—,

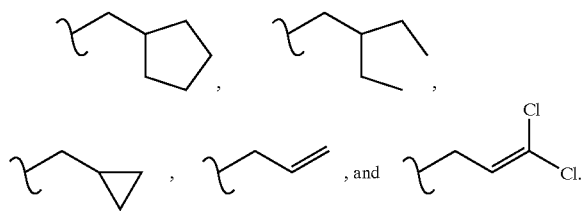

An aspect of this invention is prodrug 2, wherein $R^2$ is selected from the group consisting of

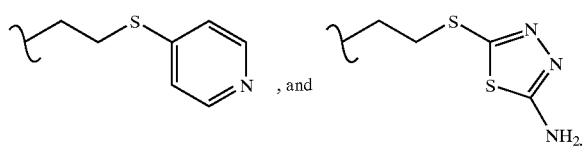

An aspect of this invention is prodrug 2, wherein $R^3$ is selected from the group consisting of

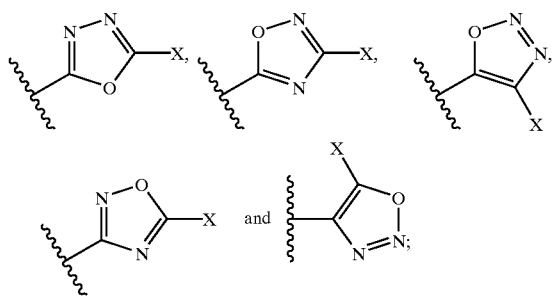

wherein X is selected from the group consisting of hydrogen, halogen, cyano, —$NH_2$, —$N(CH_3)_2$, —$NHSO_2NH_2$, —$SO_2NH_2$ and —$SCH_3$.

In the above prodrug, X is $NH_2$ in another aspect of this invention.

An aspect of this invention is prodrug 2, wherein

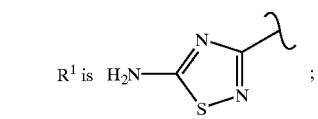

$R_2$ is hydrogen; and

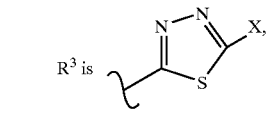

wherein X is —$NH_2$.

An aspect of this invention is prodrug 2, wherein

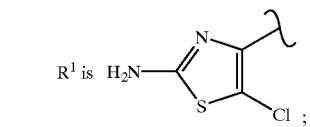

$R_2$ is hydrogen; and

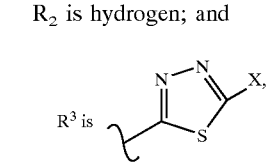

wherein X is —$NH_2$.

Pharmaceutically acceptable salts of the above compounds and prodrugs are also an aspect of this invention.

In a pharmaceutically acceptable salt, a compounds herein may be either cationic or anionic and will require an appropriately charged counter-ion. Presently preferred pharmaceutically acceptable salts include (1) inorganic salts such as sodium, potassium, ammonium, chloride, bromide, iodide, nitrate, phosphate or sulfate; (2) carboxylate salts such as acetate, propionate, butyrate, maleate, or fumarate; (3) alkylsulfonate salts such as methanesulfonate, ethanesulfonate, 2-hydroxyethylsulfonate, n-propylsulfonate or isopropylsulfonate; and (4) hydroxycarboxylate salts such as lactate, malate, and citrate. Pharmaceutically acceptable salts wherein the compound or prodrug herein forms the anionic species, usually as the carboxylate anion, are generally prepared by reacting the compound with an organic base, such as, without limitation, benzathene, procain, chloroprocaine, choline, diethanolamine, ethylenediamine, meglumine or an inorganic base such as, without limitation, lithium, sodium, potassium, magnesium, calcium, aluminum or zinc hydroxide, alkoxide, carbonate, bicarbonate, sulfate, bisulfate, amide, alkylamide, or dialkylamide.

Another aspect of this invention is a compound or prodrug of this invention, or a salt thereof, that is active against methicillin-resistant staphylococci, as demonstrated by a lower minimum inhibitory concentration than methicillin against *S. aureus* COL (Meth$^R$)(bla−), *S. aureus* 76 (Meth$^R$)(bla+), *S. aureus* ATCC 33593 (Meth$^R$), *S. aureus* Spain #356 (Meth$^R$), and *S. haemolyticus* 05 (Meth$^R$).

An aspect of this invention is a composition comprising a therapeutically effective amount of a compound or prodrug of this invention, or a salt thereof, that may be used to treat infections caused by bacteria resistant to other beta-lactam antibiotics.

An aspect of this invention is a method for treating a infection caused by bacteria resistant to existing beta-lactam antibiotics, in particular methicillin-resistant staphylococci, comprising administering a therapeutically effective amount of a compound or prodrug of this invention, or a salt thereof, to a patient suffering from such b infection.

Of course, the compounds, prodrugs and salts of the present invention may also be used as an alternative treatment for patients infected with bacteria that still are sensitive to current beta-lactam antibiotics.

In another aspect of this invention, the compounds herein may formulated with a pharmaceutically acceptable carrier or diluent for administration to a patient.

DETAILED DESCRIPTION OF THE INVENTION

Brief description of the Tables

Table 1 shows the activity of selected 3-phenylthiocephems compounds of this invention against a number of bacterial species.

Table 2 shows the activity of selected 3-(N-phenypyrazol-5-yl)thiocephems of this invention against a number of bacterial species.

Table 3 shows the activity of selected 3-(pyrid-4-yl) thiocephems of this invention against a number of bacterial species.

Table 4 shows the activity of selected 3-heteroarylthiocephems of this invention against a number of bacterial species.

Table 5 shows the activity of additional selected 3-heteroarylthiocephems of this invention against a number of bacterial species.

Definitions

The phrase "beta-lactam resistant bacteria" refers to bacteria against which a beta-lactam antibiotic has a minimum inhibitory concentration (MIC) of greater than 32 µg/mL.

A "patient" refers to any organism that is capable of being infected by a bacterium. In particular, a patient refers to a mammal and most particularly, to a human being.

A "prodrug" refers to a compound that converts to the active parent drug in vivo. Prodrugs are often useful because, for example, they may be easier to administer than the parent drug. For instance, a prodrug may be bioavailable by oral administration whereas the parent drug is not. A prodrug may also have better solubility in pharmaceutical compositions than the parent drug. An example, without limitation, of a prodrug would be an ester of a beta-lactam antibiotic wherein the free carboxylic acid is the active form. The relatively lipophilic ester can more easily traverse the bacterial cell membrane and, once it is in the interior of the cell where water solubility is beneficial, it can metabolically hydrolyze to the carboxylic acid. A further example of a prodrug would be a short peptide (polyaminoacid) wherein an terminal amino group is bonded to a carboxylic acid moiety of a compound herein or a terminal carboxylic acid group is bonded to an amino group of a compound herein and the peptide is likewise metabolized to release the active entity.

Compounds of the Invention

The present invention provides compounds, prodrugs and salts thereof for use in the treatment of bacterial infections, especially infections caused by bacteria which have developed resistance to existing beta-lactam antibiotics including conventional cephalosporins. Compositions comprising compounds, salts and prodrugs of this invention and methods for their use in the treatment of bacterial infections area also provided herein.

The compounds of the present invention may be prepared as pharmaceutically acceptable salts or, for that matter, salts that are not pharmaceutically acceptable. Any such salt is within the scope of the present invention. The salts are prepared by reacting a compound herein with an acid or a base. Suitable acids include, without limitation, trifluoroacetic acid, hydrochloric acid, methanesulfonic acid and other organic or inorganic acids. Useful bases include, without limitation, benzathene, chloroprocaine, choline, diethanolamine, ethylenediamine, meglumine, procain and lithium, sodium, potassium, magnesium, calcium, aluminum or zinc hydroxide, alkoxide, carbonate, bicarbonate, sulfate, bisulfate, amide, alkylamide or dialkylamide. A salt of a compound herein may exist as a combination of one or more equivalents of acid or base per equivalent of compound or one or more equivalents of compound per equivalent of acid or base.

Synthesis

In general, the cephalosporins of the present invention may be synthesized using well-known methods and readily available materials (see, e.g., March; Larock, COMPREHENSIVE ORGANIC TRANSFORMATIONS (VCH Publishers, 1989); G. I. Georg, THE ORGANIC CHEMISTRY OF β-LACTAMS, (VCH 1992); and, Greene and Wuts, PROTECTIVE GROUPS IN ORGANIC SYNTHESIS, 3$^{rd}$ Ed., John Wiley & Sons, New York, N.Y., 1999, each of which is incorporated herein by reference). Those skilled in the art will be able to devise numerous alternative approaches to these compounds; all such approaches are within the scope of this invention. Thus, the following synthetic schemes are presented for purpose of example only and are not to be construed as limiting this invention in any manner whatsoever.

For example, C-7 acyl intermediates may be synthesized as follows:

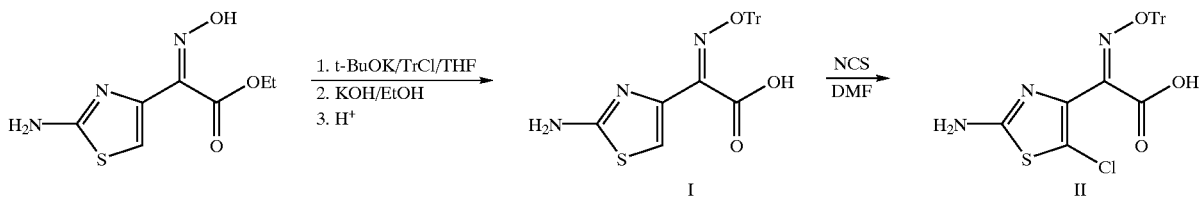

-continued

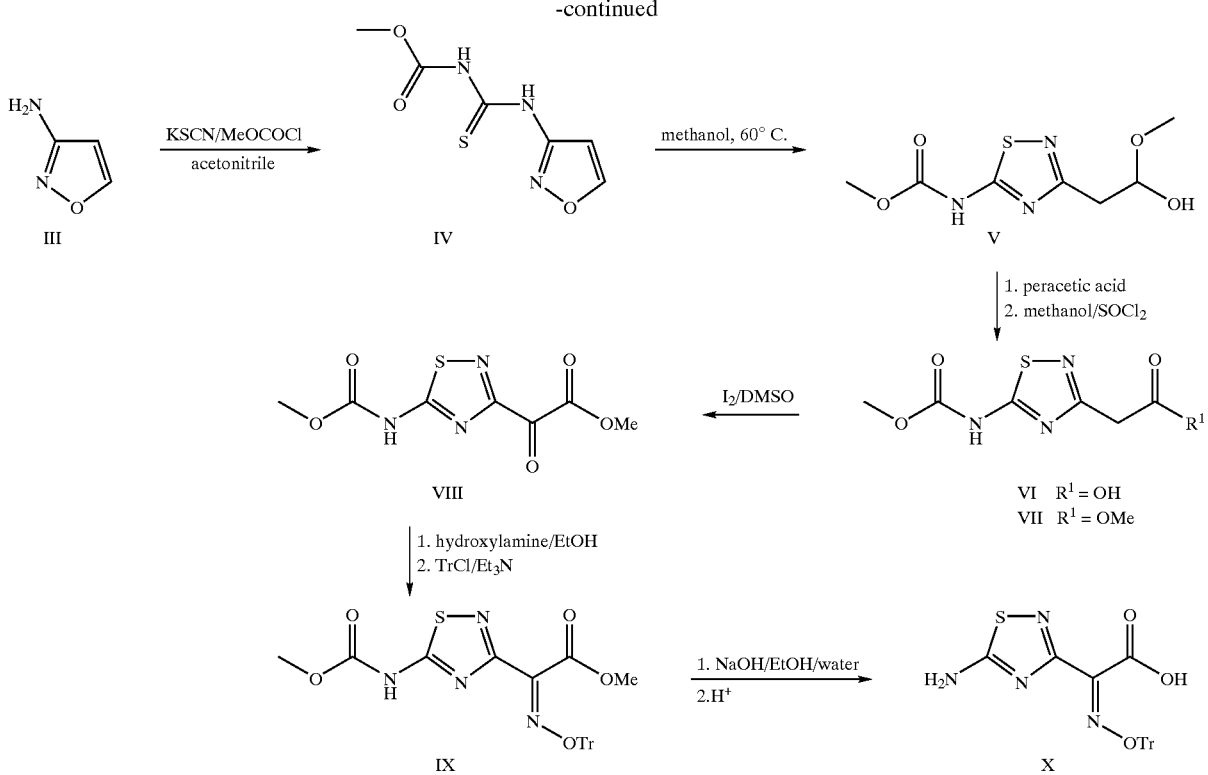

The acylamino group, $R^1$ below, can be attached to the C-7 position of a cephalosporin intermediates by a variety of well known-techniques (see, e.g., Barrett, J. C. S. Perkin I, 1629 (1979) or Chauvette, *J Org. Chem.* 36:1259 (1971). For example, a cephalosporin bearing a C-7 acylamino group, a carboxyl protecting group at $R^2$ and a leaving group at $R''^1$ can be reacted with a heterocyclic thiol:

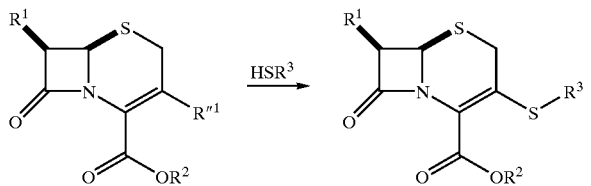

$R''^1$ is a leaving group such as, without limitation chloro, bromo, p-toluenesulfonate and other aryl sulfonates, alkyl sulfonates such as methylsulfonate and trifluoromethylsulfonate, fluorosulfonate and phosphorus derivatives such as $(R''^2O)_2PO$— in which $R''^2$ is selected from the group consisting of hydrogen and alkyl.

$R^2$ in the above reaction scheme is a carboxyl protecting group such as, without limitation, p-methoxybenzyl, benzhydryl, allyl, p-nitrobenzyl, benzyl, p- or o-nitrobenzyl, 2,2,2-trichloroethyl, allyl, cinnamyl, benzhydryl, 2-chloroallyl, t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4- or 2-methoxybenzyl, 2,4-dimethoxybenzyl, 3,4-dimethoxybenzyl, 2,4,6-trimethoxybenzyl, methoxymethyl, benzhydryl, or 3,3-dimethylallyl. Presently preferred protecting groups are t-butyl, p-methoxybenzyl, p-nitrobenzyl, allyl and benzhydryl. The protection and de-protection of carboxyl groups using these and other reagents are well known in the art (see, e.g., Greene and Wuts, supra).

The reaction may be carried out at, above or below room temperature. An organic or inorganic base may be added to facilitate reaction. If a base is added, nitrogen bases are presently preferred. Useful nitrogen bases include, without limitation, ammonia, methylamine, trimethylamine, triethylamine, aniline, 1,8-diazabicyclo[5.4.0]undec-7-ene, diisopropylethylamine, pyrrolidine, piperidine, and pyridine or substituted pyridine (e.g., 2,6-di-tert-butylpyridine). Other bases, which may be used include, without limitation, acetate, and formate anions. Useful inorganic bases include, again without limitation, hydroxide, phosphate, carbonate, bicarbonate, bisulfate, hydrosulfide, and amide anions. Those skilled in the art will be capable of selecting an appropriate base to match the requirements of the reaction conditions based on the disclosures herein.

The solvent system in which the reaction is carried out may be homogeneous or heterogeneous. By "homogeneous" is meant that the solvents used are completely miscible, that is, they form only one phase. By "heterogeneous" it is meant that the solvents are not miscible, and therefore, form more than one, usually two, phases. In many instances one of the phases is water and the other is a water immiscible organic solvent.

When a heterogeneous solvent system is used, the reaction will often be carried out in the presence of a phase transfer catalyst. Common phase transfer catalysts include, without limitation, quaternary ammonium salts.

An alternative to the above would be to add the 7-acyl substituent after the thio-linked heterocyclic substituent is attached to the cephalosporin:
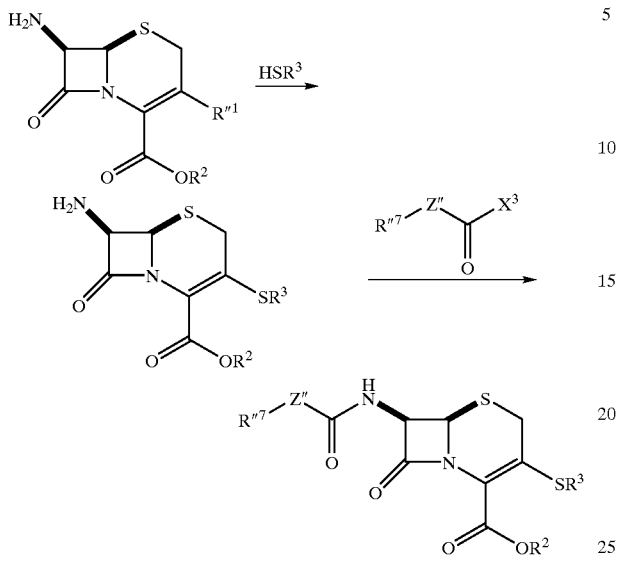
Or, the 3-thio group can be added to a molecule already having a 7-acyl substituent, which can then be further manipulated:
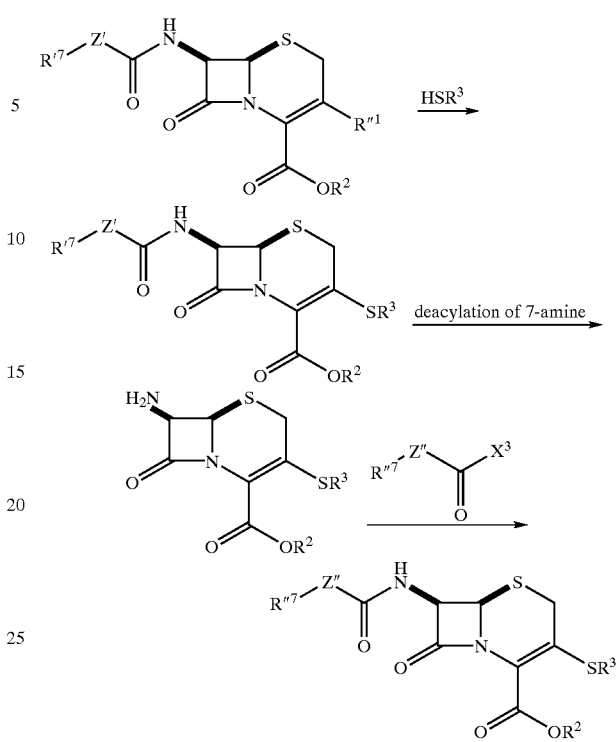
Sulfoxide cephem analogs can be synthesized as follows:
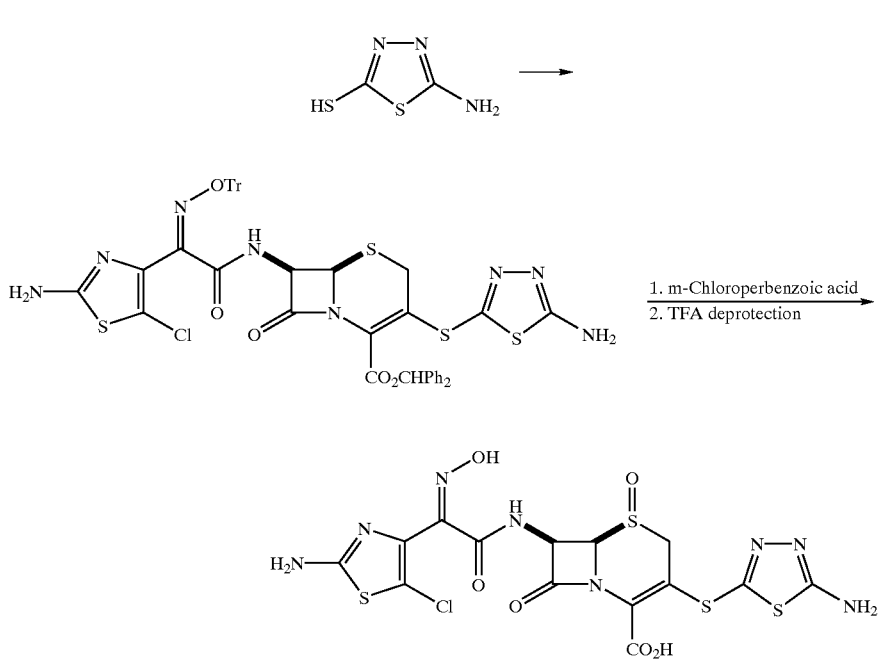

Side chains on C-7 and C-3 of the cephem core may be prepared by a variety of procedures such as those of Tatsuka, K. et al., *Bull. Chem. Soc. Jpn.,* 1994, 67, 1701–1707; Csendes, B., et al., *Journal of Antibiotics,* 1983, 36, 1020; and Bjoork, P., et al., *J. Heterocycl. Chem,* 1995. 32(3), 751, and modifications thereof.

The following synthetic scheme shows additional approaches to the preparation of the compounds of this invention:

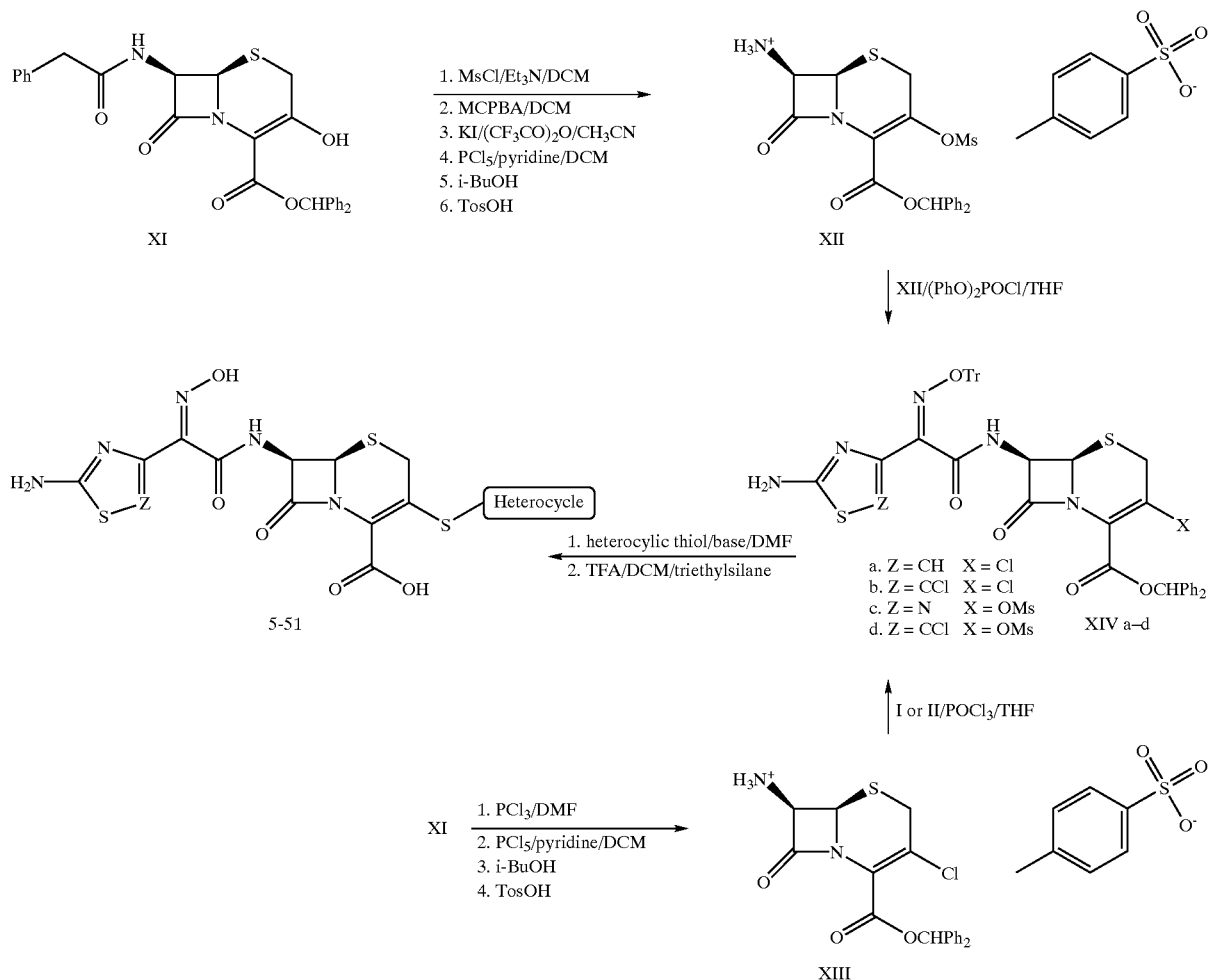

Still another synthetic approach to the compounds herein is the following:

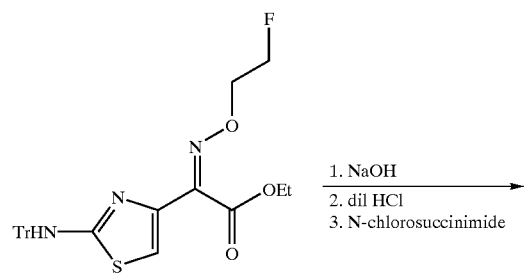

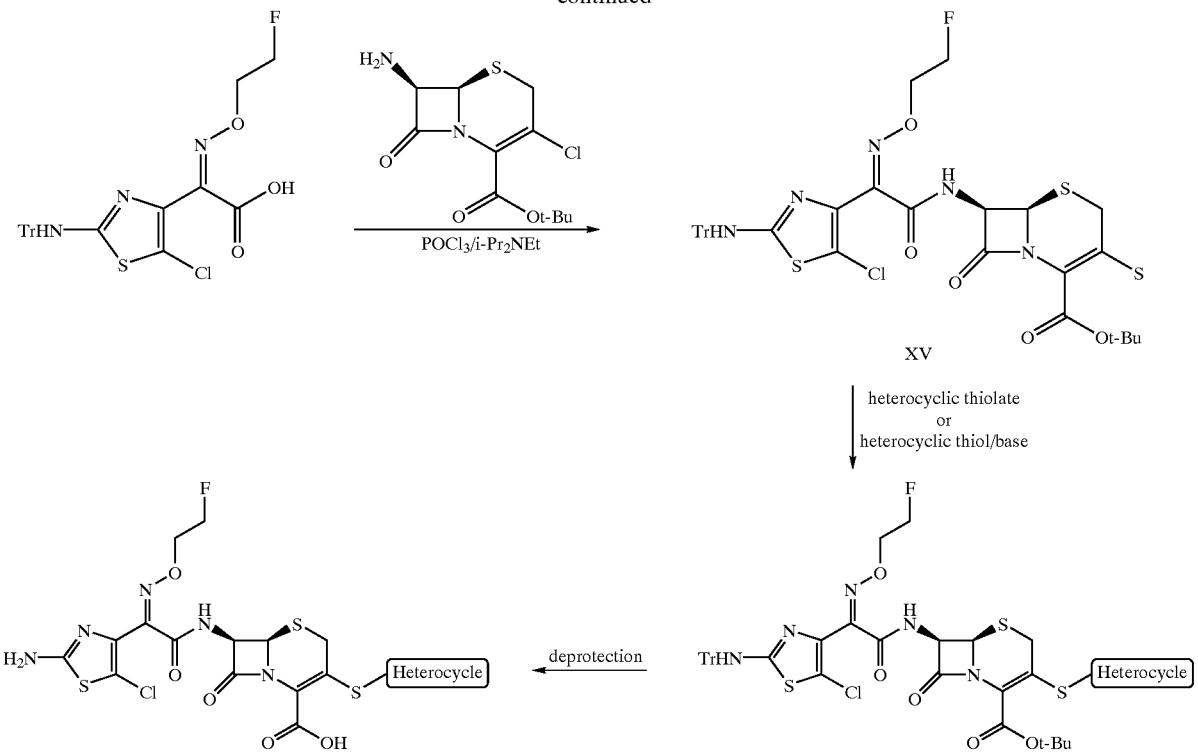
-continued
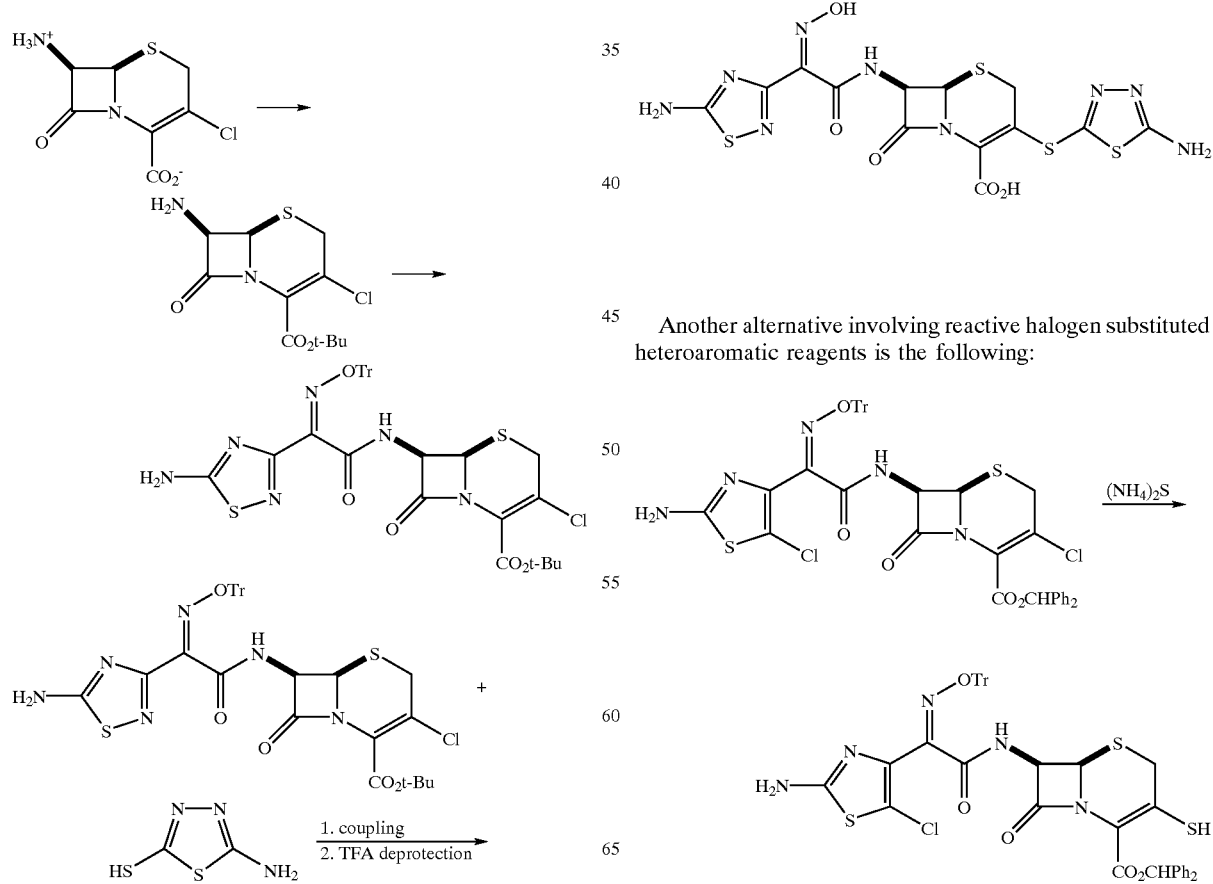
Likewise, the following procedure may be employed:
Another alternative involving reactive halogen substituted heteroaromatic reagents is the following:

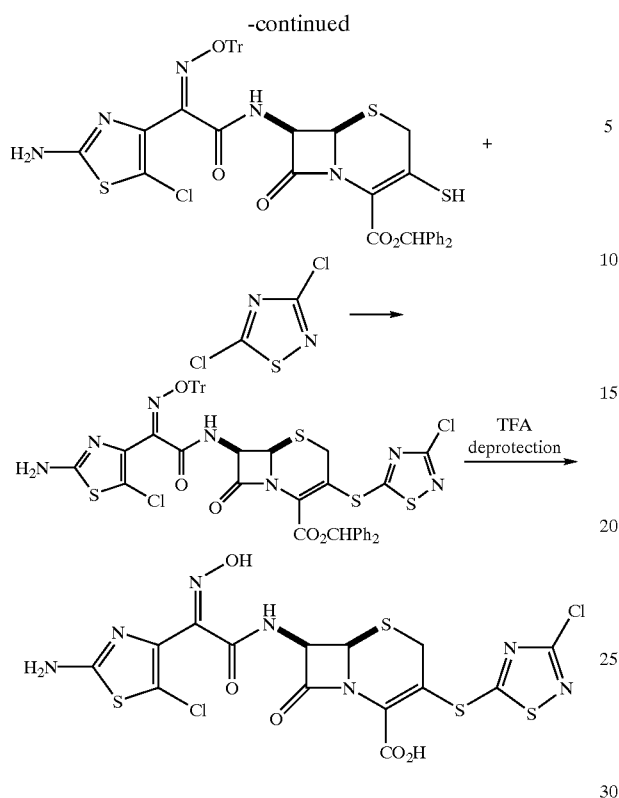

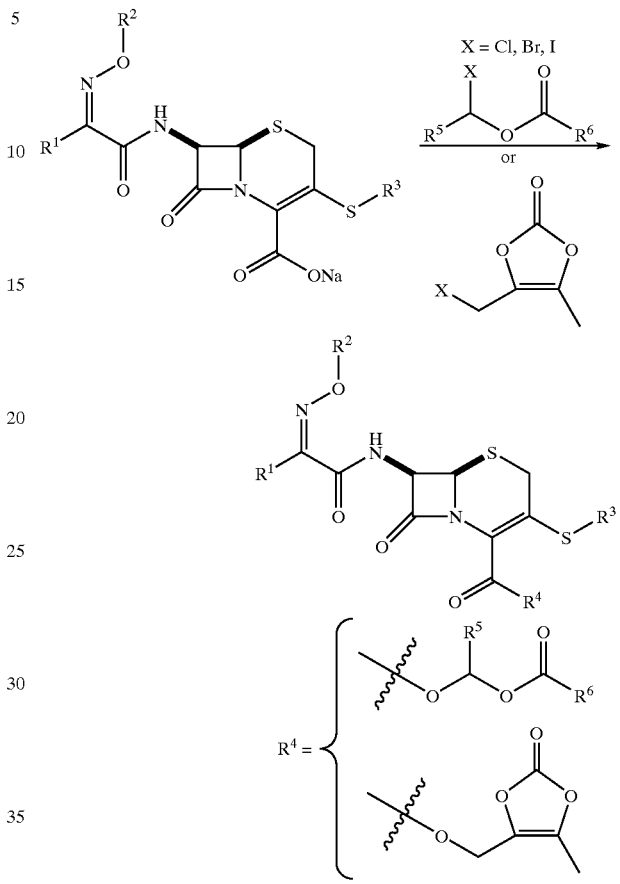

With regard to the various synthetic schemes depicted above, the following observations are noted:

The synthesis of aminothiazoleacetic acid and aminochlorothiazoleacetic acid intermediates I and II, which are used for introduction of C-7 acyl functionalities, has been previously described (U.S. Pat. No. 6,025,352). Synthesis of thiadiazoleacetic acid intermediate X was accomplished using the Katayama route as described in Tatsuta K.; Kurita Y.; Inagaki T.; Yoshida R.; Process for preparing 1,2,4-Thiadiazole Derivatives. EP 0 536 900 A2, Sep. 10, 1992. It starts with 3-aminoisoxazole III, which is converted to thiourea IV by reaction with in situ generated carbomethoxythiocyanate. Thermal rearrangement to amiothiadiazole derivative V followed by aldehyde oxidation and acid esterification produces aminothiadiazoleacetic acid methyl ester VII. Oxidation of VII with iodine/dimethyl sulfoxide produces ketoester VIII. In the subsequent oxime formation step, the desired syn-oxime is accompanied by its anti-oxime isomer in an approximately 7:1 ratio. However, after the O-tritylation step, the syn-oxime ester IX can be crystallized from the crude reaction mixture and isolated in a relatively pure state. Careful hydrolysis of IX gives the crystallizable sodium salt of the acid X without extensive degradation of the thiadiazole ring.

Acids I, II and X were coupled to benzhydryl protected 7-amino-3-methanesulfonyloxy-(XII) or 7-amino-3-chloro-(XIII) to give the amides XIV a-d. In the subsequent reaction with heterocyclic thiol, base-induced isomerization to the undesired $\Delta^2$ cephem isomer (up to 80%) often could not be suppressed, and the desired $\Delta^3$ isomers of the protected 3-heteroarylthiocephems had to be isolated by chromatography. The final 3-heteroarylthiocephalosporins 5–53 were obtained by de-protection with trifluoroacetic acid and, in some cases, were converted into the corresponding sodium salts.

Prodrugs of the compounds herein are prepared by reacting the carboxylic acid group as, for example, the sodium salt, with an alkyl halide:

Pharmaceutical Applications and Preparations

A therapeutically effective amount of a compound of this invention can be used to treat a patient suffering from a beta-lactam resistant bacterial infection such as, without limitation, a methicillin-resistant, vancomycin-resistant or ampicillin-resistant infection. In particular resistant S. aureus infections may be treated. Especially important are infections caused by strains such as S. aureus Col (Meth$^R$) (bla–), S. aureus 76 (Meth$^R$) (bla+), E. fœcium ATCC 35667, or E. fœcalis ATCC 29212. Of course, the compounds will also be effective against bacteria that are also sensitive to methicillin, vancomycin, and/or ampicillin.

A composition containing a compound of this invention can be administered therapeutically or prophylactically. In therapeutic applications, a therapeutically effective amount of the composition is administered to a patient already suffering from an infection to cure or at least partially arrest the symptoms of the infection. What constitutes a "therapeutically effective amount" will depend on the activity of the compound being administered, on the severity and course of the infection, on previous therapy, on the patient's health status and response to the drugs, and on the judgment of the treating physician. In prophylactic applications, a composition containing a compound or compounds of this invention is administered to a patient not yet infected but at particular risk of infection. Such patients include, for example and without limitation, immuno-compromised individuals. Prophylactic amounts may also be given to a patient who has already received a therapeutic amount of the composition and whose condition has improved to the point that a lesser amount may be administered for the purpose of preventing recurrence of the infection. The dosage or the frequency of administration, or both, can be reduced, as a function of the symptoms, to a level at which the improved condition is retained. Again, the precise amount that will achieve a prophylactically effective amount will depend on the patients state of health, weight, and the like.

Or, when the symptoms have been alleviated to the desired level, treatment can cease. Patients can, however, require intermittent treatment on a long-term basis upon any recurrence of the disease symptoms.

In general, a suitable effective dose of a compound of this invention will be in the range of 0.1 to 10000 milligram (mg) per day, preferably in the range of 20 to 2000 mg per day. The desired dosage may be administered in one, two, three, four or more sub-doses administered at appropriate intervals throughout the day. Preferably, the compounds of this invention will be administered in amounts from about 2.0 mg/kg to 250 mg/kg of patient body weight, between about one and four times per day.

While it is possible to administer a compound of this invention alone, it is preferable to present it in a pharmaceutically acceptable formulation. Such a formulation will comprise a therapeutically or prophylactically effective amount of one or more compounds of this invention together with one or more pharmaceutically acceptable carriers. Carriers include, without limitation, solid materials such as starch, lactose, dicalcium phosphate, microcrystalline cellulose, sucrose, and kaolin or liquid such as, without limitation, sterile water, polyethylene glycols, non-ionic surfactants, and edible oils such as corn, peanut and sesame oils. In addition, various adjuvants such as, without limitation, flavoring agents, coloring agents, preservatives, and antioxidants, e.g., vitamin E, ascorbic acid, BHT or BHA may be included in the formulation. Various other formulation possibilities are described in Goodman and Gilman, *The Pharmacological Basis of Therapeutics,* 8th Ed. (1990), Pergamon Press; and Remington's Pharmaceutical Sciences, 18th ed., Mack Publishing Co., Easton, Pa. (1990). Methods of administration, for example without limitation, oral, intravenous, intraperitoneal, or intramuscular are also discussed in those references. Pharmaceutically acceptable carriers are also described in the MERCK INDEX, Merck & Co., Rahway, N.J.

Formulations of this invention can be prepared, for example, in solid, semi-solid or liquid form, such as, without limitation, tablets, pills, powders, solutions, suspensions, liposomes, etc. The preferred form will depend on the intended mode of administration and the therapeutic application. A pharmaceutically acceptable salt of the compound may be used to simplify preparation of the composition. Preferred salts include those of sodium, potassium, arginine, glycine, alanine, threonine, and lysine. These may be prepared in water containing a surfactant such as hydroxypropylcellulose.

Depending on the specific conditions being treated, the compounds, prodrugs and salts of this invention may be administered systemically or locally. Techniques for formulation and administration may be found in Remington's Pharmaceutical Sciences, supra. Suitable routes of administration include, without limitation, oral, rectal, transdermal, vaginal, transmucosal, parenteral, intramuscular, subcutaneous, intramedullary, intrathecal, intraventricular, intravenous, intraperitoneal, intranasal and intraocular.

For injection, the compounds, prodrugs and salts of this invention may be formulated in aqueous solutions, preferably in physiologically compatible buffers such as Hanks' solution, Ringer's solution, or physiological saline buffer.

For transmucosal administration, penetrants appropriate to the barrier to be permeated are used in the formulation. Such penetrants are generally known in the art. In soft capsules, the active compounds may be dissolved or suspended in suitable liquids, such as fatty oils, liquid paraffin, or liquid polyethylene glycols. In addition, stabilizers may be added.

Biological Activity

The following tables show the activity of a number of representative compounds of this invention against a variety of bacteria including some that are resistant to present clinical β-lactam antibiotics:

TABLE 1

Substituted 3-phenylthiocephems

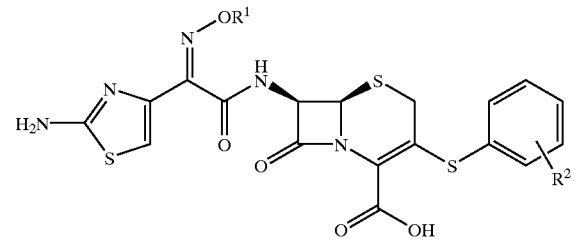

| Compound No. | $R^1$ | $R^2$ | S. a. Smith | S. a. 29213 | S. a. COL | S. a. 76 | E. f. 29212 | E. f. 35667 | $ED_{50}$, mg/kg (95% C.I.) |
|---|---|---|---|---|---|---|---|---|---|
| Imipenem | — | — | 0.25 | <0.02 | 16 | 32 | 1 | 4 | 0.15 (0.06–0.25) |
| Vancomycin | — | — | 0.5 | 0.5 | 1 | 0.5 | 1 | 0.25 | 2.1 (1.3–2.9) |
| 5 | methyl | 2-bromo | — | 0.5 | 16 | 16 | >32 | 32 | — |
| 6 | methyl | 4-bromo | — | <0.015 | — | 32 | 16 | 16 | — |
| 7 | H | 2-iodo | — | <0.25 | 2 | 4 | — | 2 | — |

MIC (μg/mL)

TABLE 1-continued

Substituted 3-phenylthiocephems

| Compound No. | R¹ | R² | MIC (μg/mL) | | | | | | ED₅₀, mg/kg (95% C.I.) |
|---|---|---|---|---|---|---|---|---|---|
| | | | S. a. Smith | S. a. 29213 | S. a. COL | S. a. 76 | E. f. 29212 | E. f. 35667 | |
| 8 | methyl | 2-iodo | — | 1 | 32 | 32 | — | 32 | — |
| 9 | cyclopentyl | 2-iodo | — | <0.25 | 1 | 2 | 2 | 2 | — |
| 10 | H | 2-phenyl | — | 0.5 | 4 | 8 | 2 | 2 | — |
| 11 | 3,3-dichloro-propen-2-yl | 2-iodo | — | — | 2 | 2 | 4 | 8 | — |
| 12 | cyclopentyl | 2-cyano | — | 1 | 4 | 8 | 8 | 8 | — |

Abbreviations: S. a. Smith, *Staphylococcus aureus* Smith (MSSA); S. a. 29213, *Staphylococcus aureus* ATCC 29213 (MSSA); S. a. COL, *Staphylococcus aureus* COL (MRSA, non-β-lactamase producing); S. a. 76, *Staphylococcus aureus* 76 (MRSA, β-lactamase producing); E. f. 29212, *Enterococcus faecalis* ATCC 29212; E. f. 35667, *Enterococcus faecium* ATCC 35667; $ED_{50}$, 50% efficacious dose, *S. aureus* Smith, mg/kg; 95% C.I.-95% confidence interval.

TABLE 2

Substituted 3-(N-phenylpyrazol-5-yl)thiocephems

| Compound No. | R¹ | R² | MIC (μg/mL) | | | | | | $ED_{50}$, mg/kg |
|---|---|---|---|---|---|---|---|---|---|
| | | | S. a. Smith | S. a. 29213 | S. a. COL | S. a. 76 | E. f. 29212 | E. f. 35667 | |
| 13 | Cyclopentyl | H | 0.5 | 0.5 | 2 | 4 | 2 | 4 | >10 |
| 14 | 2-fluoroethyl | H | — | 1 | 8 | 16 | 32 | 16 | — |
| 15 | H | H | — | 1 | 16 | 32 | 2 | 8 | — |
| 16 | 2-fluoroethyl | Cl | 0.5 | 0.5 | 2 | 4 | 1 | 4 | — |
| 17 | 1-ethylpropyl | H | — | 0.5 | 2 | 4 | 2 | 4 | >10 |
| 18 | 1,1-dimethylethyl | H | 1 | 1 | 8 | 16 | 2 | 16 | |
| 19 | Cyclopropylmethyl | H | 0.5 | 0.5 | 4 | 8 | 16 | 16 | >10 |
| 20 | 2-propenyl | H | 0.5 | 1 | 8 | 16 | 32 | 32 | — |

Abbreviations: S. a. Smith, *Staphylococcus aureus* Smith (MSSA); S. a. 29213, *Staphylococcus aureus* ATCC 29213 (MSSA); S. a. COL, *Staphylococcus aureus* COL (MRSA, non-β-lactamase producing); S. a. 76, *Staphylococcus aureus* 76 (MRSA, β-lactamase producing); E. f. 29212, *Enterococcus faecalis* ATCC 29212; E. f. 35667, *Enterococcus faecium* ATCC 35667; $ED_{50}$, 50% efficacious dose, *S. aureus* Smith, mg/kg.

TABLE 3

Substituted 3-(pyrid-4-yl)thiocephems

[Structure: 7-[(Z)-2-(2-aminothiazol-4-yl)-2-(hydroxyimino)acetamido]-3-(pyrid-4-ylthio)cephem-4-carboxylic acid with R² on thiazole and R¹ on pyridine]

| Compound No. | R¹ | R² | MIC (µg/mL) S. a. Smith | S. a. 29213 | S. a. COL | S. a. 76 | E. f. 29212 | E. f. 35667 | HSB (HSB*) | ED₅₀, mg/kg (95% C.I.) |
|---|---|---|---|---|---|---|---|---|---|---|
| RWJ 54428 | -CH₂-S-CH₂CH₂-NH₃⁺ | Cl | 0.125 | 0.25 | 0.5 | 1 | 0.06 | 0.25 | 84% (67%) | 1.0 (0.7–1.6) |
| 21 | H | Cl | 0.25 | 0.25 | 2 | 2 | 0.5 | 2 | 98% | 3.6 (1.1–6.7) |
| 22 | -CH₂-S-CH₂-C(=O)NH₂ | Cl | 0.25 | 0.5 | 4 | 4 | 0.5 | 1 | 94% (88%) | 1.15 (0.7–1.6) |
| 23 | -CH₂-S-CH₂CH₂-NH-CHO | H | 0.5 | 0.5 | 8 | 8 | 0.5 | 4 | 86% | — |
| 24 | -CH₂-S-CH₂CH₂-NH-CHO | Cl | 0.25 | 0.5 | 2 | 2 | 0.125 | 0.5 | 95% (88%) | >5 |
| 25 | -CH₂-S-(pyrid-4-yl) | Cl | 0.25 | 0.25 | 1 | 2 | 0.125 | 0.25 | >99% | >5 |
| 26 | -CH₂-S-(5-amino-1,3,4-thiadiazol-2-yl) | Cl | 0.06 | 0.25 | 1 | 2 | 0.25 | 0.5 | >99% | 0.38 (01–0.7) |
| 27 | -S-CH₂CH₂-NH-CHO | Cl | 0.25 | 0.25 | 2 | 4 | 0.25 | 1 | 94% | 2.27 (1.0–5.5) |
| 28 | hydroxymethyl | Cl | 0.125 | 0.5 | 2 | 2 | 0.25 | 1 | >99% | — |
| 29 | -CH₂-S-(2-aminopyrid-3-yl) | Cl | 0.25 | 0.125 | 1 | 2 | 0.125 | 0.5 | — | >5 |

TABLE 3-continued

Substituted 3-(pyrid-4-yl)thiocephems

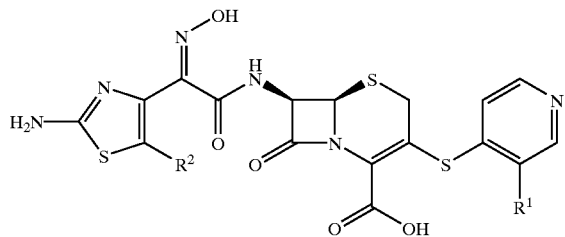

| Compound No. | R[1] | R[2] | MIC (μg/mL) | | | | | | HSB (HSB*) | ED$_{50}$, mg/kg (95% C.I.) |
| | | | S. a. Smith | S. a. 29213 | S. a. COL | S. a. 76 | E. f. 29212 | E. f. 35667 | | |
|---|---|---|---|---|---|---|---|---|---|---|
| 30 | ![structure] | Cl | 0.5 | 0.5 | 4 | 4 | 0.125 | — | 96% | — |

Abbreviations: S. a. Smith, *Staphylococcus aureus* Smith (MSSA); S. a. 29213, *Staphylococcus aureus* ATCC 29213 (MSSA); S. a. COL, *Staphylococcus aureus* COL (MRSA, non-β-lactamase producing); S. a. 76, *Staphylococcus aureus* 76 (MRSA, β-lactamase producing); E. f. 29212, *Enterococcus faecalis* ATCC 29212; E. f. 35667, *Enterococcus faecium* ATCC 35667; HSB, human serum binding; HSB*, human serum binding calculated using serum effect on MIC; ED$_{50}$, 50% efficacious dose, *S. aureus* Smith, mg/kg; 95% C.I - 95% confidence interval.

TABLE 4

Substituted 3-heteroarylthiocephems

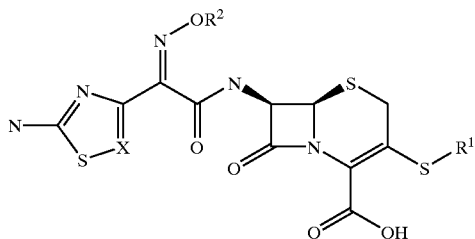

| Compound No. | R[1] | R[2] | X | MIC (μg/mL) | | | | | | HSB (HSB*) |
| | | | | S. a. Smith | S. a. 29213 | S. a. COL | S. a. 76 | E. f. 29212 | E. f. 35667 | |
|---|---|---|---|---|---|---|---|---|---|---|
| 31 | ![imidazole] | H | CCl | 0.125 | 0.5 | 16 | 32 | 1 | 16 | — |
| 32 | ![imidazole] | H | CCl | 0.125 | 0.25 | 32 | >32 | 2 | 16 | — |
| 33 | ![thiadiazole] | H | CCl | 0.5 | 1 | 4 | 8 | 1 | 4 | — |
| 34 | ![thiadiazole] | H | CCl | 0.125 | 0.125 | 2 | 2 | 0.25 | 2 | — (98%) |

TABLE 4-continued

Substituted 3-heteroarylthiocephems

| Compound No. | R¹ | R² | X | MIC (μg/mL) | | | | | | HSB (HSB*) |
|---|---|---|---|---|---|---|---|---|---|---|
| | | | | S. a. Smith | S. a. 29213 | S. a. COL | S. a. 76 | E. f. 29212 | E. f. 35667 | |
| 35 | methyl-triazolopyridine | H | CCl | 0.25 | 0.5 | 4 | 4 | 0.25 | 4 | — (88%) |
| 36 | 5-methyl-2-amino-1,3,4-thiadiazole | H | CCl | 0.25 | 0.25 | 1 | 2 | 0.25 | 1 | 90% (94%) |
| 37 | 5-methyl-2-amino-1,3,4-thiadiazole | H | N | 0.125 | 0.25 | 4 | 4 | 2 | 1 | 79% (50%) |
| 38 | 2-amino-4,5-dimethylthiazole | H | CCl | 0.125 | 0.125 | 2 | 8 | 1 | 4 | — (97%) |
| 39 | 4-methyl-1,2,3-thiadiazole | H | N | 0.125 | 0.125 | 8 | 8 | 1 | 2 | — (94%) |
| 40 | 3-methyl-1,2,4-triazole | H | CCl | 0.5 | 0.25 | 8 | 8 | 1 | 4 | 92% (88%) |
| 41 | 5-methyl-1,3,4-thiadiazole | H | CCl | 0.125 | 0.125 | 1 | 1 | 0.25 | 0.5 | 91% (98%) |
| 42 | 5-methyl-2-amino-1,3,4-thiadiazole | 3-fluoropropyl | CCl | 0.25 | 0.5 | 2 | 2 | 1 | 4 | 65% (75%) |

Abbreviations: S. a. Smith, *Staphylococcus aureus* Smith (MSSA); S. a. 29213, *Staphylococcus aureus* ATCC 29213 (MSSA); S. a. COL, *Staphylococcus aureus* COL (MRSA, non-β-lactamase producing); S. a. 76, *Staphylococcus aureus* 76 (MRSA, β-lactamase producing); E. f. 29212, *Enterococcus faecalis* ATCC 29212; E. f. 35667, *Enterococcus faecium* ATCC 35667; HSB, human serum binding ; HSB*, human serum binding calculated using serum effect on MIC.

TABLE 5

Substituted 3-heteroarylthiocephems

| Compound No. | R¹ | R² | Z | X | S. a. Smith | S. a. 29213 | S. a. COL | S. a. 76 | E. f. 29212 | E. f. 35667 | HSB (HSB*) |
|---|---|---|---|---|---|---|---|---|---|---|---|
| 43 | 5-methyl-1,3,4-thiadiazol-2-yl (S-N=N, methyl) | H | — | CCl | 0.06 | <0.06 | 0.5 | 1 | 0.125 | 0.5 | 96% (−) |
| 44 | 5-methyl-2-(methylthio)-1,3,4-thiadiazol-... | H | — | CCl | — | 0.25 | 1 | 1 | 0.25 | 1 | — |
| 45 | 3,5-dimethyl-1,2,4-oxadiazol-... | H | — | CCl | 1 | 0.5 | 4 | 4 | 0.125 | 0.5 | — |
| 46 | 2,5-dimethyl-1,3,4-oxadiazol-... | H | — | CCl | — | 0.5 | 4 | 4 | 0.5 | 4 | — |
| 47 | 3-amino-5-methyl-1,2,4-thiadiazol-... | H | — | CCl | 0.25 | 0.125 | 0.5 | 1 | 0.125 | 0.5 | — |
| 48 | 5-methyl-1,3,4-oxadiazol-... | H | — | CCl | — | 0.25 | 2 | 2 | 0.25 | 1 | — |
| 49 | 2-amino-5-methyl-1,3,4-thiadiazol-... | H | — | CH | — | 0.25 | 4 | 8 | 0.5 | 1 | — |
| 50 | 2-methyl-1,3,4-thiadiazol-... | H | — | N | — | 0.25 | 4 | 8 | 1 | 2 | — |
| 51 | 2-amino-5-methyl-1,3,4-thiadiazol-... | esoxymino | — | CH | 0.06 | 0.125 | 4 | 16 | 2 | 4 | — |
| 52 | 3-chloro-5-methyl-1,2,4-thiadiazol-... | H | — | CCl | — | 0.25 | 1 | 2 | 0.25 | 1 | — |

TABLE 5-continued

Substituted 3-heteroarylthiocephems

| Compound No. | $R^1$ | $R^2$ | Z | X | S. a. Smith | S. a. 29213 | S. a. COL | S. a. 76 | E. f. 29212 | E. f. 35667 | HSB (HSB*) |
|---|---|---|---|---|---|---|---|---|---|---|---|
| 53 | (5-methyl-2-amino-[1,3,4]thiadiazol) | H | =O | CCl | — | | | | | | — |

Abbreviations: S. a. Smith, *Staphylococcus aureus* Smith (MSSA); S. a. 29213, *Staphylococcus aureus* ATCC 29213 (MSSA); S. a. COL, *Staphylococcus aureus* COL (MRSA, non-β-lactamase producing); S. a. 76, *Staphylococcus aureus* 76 (MRSA, β-lactamase producing); E. f. 29212, *Enterococcus faecalis* ATCC 29212; E. f. 35667, *Enterococcus faecium* ATCC 35667; HSB, human serum binding; HSB*, human serum binding calculated using serum effect on MIC.

EXAMPLES

Chemical

The following chemical syntheses of some of the compounds of this invention are provided for the purpose of illustration only and are not to be construed as limiting the scope of this invention in any manner whatsoever.

(7R)-7-[2-(2-Amino-5-chlorothiazol-4-yl)-2-trityloxyiminoacetylamino]-3-(4-methyl-[1,2,3]thiadiazol-5-ylsulfanyl)-8-oxo-5-thia-1-aza-bicyclo[4.2.0]oct-2-ene-2-carboxylic acid benzhydryl ester To a stirred solution of sodium 4-methyl-[1,2,3]thiadiazole-5-thiolate (330 mg, 2.17 mmol) in DMF (5 mL) was added at room temperature 3-methanesulfonyloxycephem XIVd (1.98 g, 2.17 mmol). After 1 h the reaction mixture was partitioned between ethyl acetate and water, and the organic layer was dried over anhydrous sodium sulfate. After evaporating the solvent under reduced pressure the residue was chromatographed on silica gel column (ethyl acetate/hexane 1:1) to give the title compound (990 mg, 48%). $^1$H NMR (CDCl$_3$) δ 2.45 (s, 3H); 2.98 (d, 1H, J=16 Hz); 3.18 (d, 1H, J=16 Hz); 5.02 (d, 1H, J=6 Hz); 5.98 (d, 1H, J=6 Hz); 6.92 (s, 1H); 7.10–7.40 (m, 25H).

(7R)-7-[2-(2-Amino-5-chlorothiazol-4-yl)-2-hydroxyiminoacetylamino]-3-(4-methyl-[1,2,3]thiadiazol-5-ylsulfanyl)-8-oxo-5-thia-1-aza-bicyclo[4.2.0]oct-2-ene-2-carboxylic acid (34)

To a solution of (7R)-7-[2-(2-amino-5-chlorothiazol-4-yl)-2-trityloxyiminoacetylamino]-3-(4-methyl-[1,2,3]thiadiazol-5-ylsulfanyl)-8-oxo-5-thia-1-aza-bicyclo[4.2.0]oct-2-ene 2-carboxylic acid benzhydryl ester (990 mg, 1.05 mmol) in dichloromethane (21 mL) was added triethylsilane (11 mL) followed by addition of trifluoroacetic acid (21 mL). After 1 hr at room temperature the reaction mixture was concentrated under vacuum. Diisopropyl ether was added to the oily residue. The title compound precipitated and was filtered, washed with additional diisopropyl ether and dried under vacuum (528 mg, 95%).

$^1$H NMR (CD$_3$OD) δ 2.65 (s, 3H); 3.30 (d, 1H, J=16 Hz); 3.60 (d, 1H, J=16 Hz); 5.22 (d, 1H, J=6 Hz); 5.98 (d, 1H, J=6 Hz).

(7R)-7-[2-(2-Amino-5-chlorothiazol-4-yl)-2-trityloxyimino-acetylamino]-3-(5-amino-[1,3,4]thiadiazol-2-ylsulfanyl)-8-oxo-5-thia-1-aza-bicyclo[4.2.0]oct-2-ene-2-carboxylic acid benzhydryl ester To a stirred solution of sodium 5-amino-[1,3,4]thiadiazole-2-thiolate (100 mg, 0.64 mmol) in DMF (5 mL) at 0° C. was added 3-chloro cephem XIVb (1.98 g, 2.17 mmol). After 0.5 hour at 0° C., the reaction mixture was partitioned between ethyl acetate and water, and the organic layer was dried over anhydrous sodium sulfate. After evaporating the solvent under reduced pressure the title compound was isolated by radial chromatography on silica gel (ethyl acetate/hexane 5:1) (150 mg, 33%).

$^1$H NMR (CDCl$_3$/CD$_3$OD) δ 3.08 (d, 1H, J=16 Hz); 3.14 (d, 1H, J=16 Hz); 4.96 (d, 1 H, J=6 Hz); 5.95 (d, 1H, J=6 Hz); 6.80 (s, 1H); 7.10–7.40 (m, 25H).

(7R)-7-[2-(2-amino-5-chlorothiazol-4-yl)-2-hydroxyiminoacetylamino]-3-(5-amino-[1,3,4]thiadiazol-2-ylsulfanyl)-8-oxo-5-thia-1-aza-bicyclo[4.2.0]oct-2-ene-2-carboxylic acid (36)

To a solution of (7R)-7-[2-(2-amino-5-chloro-thiazol-4-yl)-2-trityloxyiminoacetylamino ]-3-(5-amino-[1,3,4]thiadiazol-2-ylsulfanyl)-8-oxo-5-thia-1-aza-bicyclo[4.2.0]oct-2-ene-2-carboxylic acid benzhydryl ester (150 mg, 0.17 mmol) in dichloromethane (7.5 mL) was added triethylsilane (1.5 mL). The mixture was cooled to 0° C. and trifluoroacetic acid (7.5 mL) was added. After 2 hr at 0° C. the reaction mixture was concentrated under vacuum and disopropyl ether was added to the oily residue. The title compound precipitated and was filtered, washed with additional diisopropyl ether and dried under vacuum (85 mg, 65%).

(7R)-7-[2-(2-Amino-5-chlorothiazol-4-yl)-2-hydroxyiminoacetylamino]-3-(5-amino-[1,3,4]thiadiazol-2-ylsulfanyl)-8-oxo-5-thia-1-aza-bicyclo[4.2.0]oct-2-ene-2-carboxylic acid sodium salt (36 sodium salt)

(7R)-7-[2-(2-Amino-5-chlorothiazol-4-yl)-2-hydroxyiminoacetylamino]-3-(5-amino-[1,3,4]thiadiazol-2- ylsulfanyl)-8-oxo-5-thia-1-aza-bicyclo[4.2.0]oct-2-ene-2-carboxylic acid (85 mg, 0.11 mmol) was dissolved in water (2.0 mL) and the pH was adjusted to 6.0 with 1.0 M aqueous sodium bicarbonate. The solution was loaded onto an HP20 column and inorganics were removed by washing the column thoroughly with water. The title compound was isolated by eluting with 2:1 acetonitrile/water, removing acetonitrile under reduced pressure and lyophilizing the remaining mixture (60 mg, 63%).

$^1$H NMR (D$_2$O) δ 3.30 (d, 1H, J=16 Hz); 3.60 (d, 1H, J=16 Hz); 5.18 (d, 1H, J=6 Hz); 5.80 (d, 1H, J=6 Hz).

(7R)-7-[2-(5-Amino-[1,2,4]thiadiazol-3-yl)-2-trityloxyimino-acetylamino]-3-methanesulfonyloxy-8-oxo-5-thia-1-aza-bicyclo[4.2.0]oct-2-ene-2-carboxylic acid benzhydryl ester (XIVc)

To a suspension of tosylate salt XII (1.71 g, 3.98 mmol) and acid X (2.52 g, 3.98 mmol) in THF (40 mL) at −50° C. was added diisopropylethylamine (2.08 mL, 11.94 mmol) followed by addition of phosphorous oxychloride (0.52 mL, 3.98 mmol). The reaction mixture was stirred for 1.5 hr at −35° C. and quenched with 1.0 M aqueous HCl. After partitioning between water and ethyl acetate, the organic layer was dried over anhydrous sodium sulfate and the solution was passed through a short silica gel plug. After evaporation of solvent under reduced pressure yellowish the title compound was obtained as a foam (2.68 g, 77%).

$^1$H NMR (CDCl$_3$/CD$_3$OD) δ 2.77 (s,3H); 3.40 (d, 1H, J=16 Hz); 3.70 (d, 1H, J=16 Hz); 5.11 (d, 1H, J=8 Hz); 5.98 (d, 1H, J=8 Hz); 6.83 (s, 1H); 7.10–7.30 (m, 25H).

(7R)-7-[2-(5-Amino-[1,2,4]thiadiazol-3-yl)-2-hydroxyimino-acetylamino]-3-(5-amino-[1,3,4]thiadiazol-2-ylsulfanyl)-8-oxo-5-thia-1-aza-bicyclo[4.2.0]oct-2-ene-2-carboxylic acid (37)

To a solution of 2-amino-5-mercapto-1,3,4-thiadiazole sodium salt (16 mg, 0.11 mmol) in DMF (1.0 mL) was added cephem XIVc (86 mg, 0.10 mmol). After 20 min. the reaction mixture was partitioned between dilute hydrochloric acid and ethyl acetate. The organic layer was dried over anhydrous sodium sulfate and then concentrated under reduced pressure. The desired Δ$_3$ isomer was isolated using silica gel radial chromatography (ethyl acetate/hexane 4:1). After evaporation of solvent under reduced pressure, a yellowish foam comprising the title compound was obtained (11 mg, 11%). $^1$H NMR (CDCl$_3$/CD$_3$OD) δ 3.30 (d, 1H, J=16 Hz); 3.39 (d, 1H, J=16 Hz); 5.05 (d, 1H, J=8 Hz); 5.98 (d, 1H, J=8 Hz); 6.88 (s, 1H); 7.10–7.30 (m, 25H).

Treatment with dichloromethane/trifluoroacetic acid/Et$_3$SiH (20:20:5, 1.0 mL) for 1 hr at ambient temperature was followed by concentration under reduced pressure and precipitation with diisopropyl ether/hexane. A quantitative yield of trifluoroacetate salt of cephem 37 was obtained. After dissolving in dilute sodium bicarbonate solution, sodium salt of cephem 37 was loaded on an HP20 column and isolated by elution with water/acetonitrile followed by lyopholization.

$^1$H NMR (D$_2$O) δ 3.15 (d, 1H, J=16 Hz); 3.62 (d, 1H, J=16 Hz); 5.18 (d, 1H, J=8 Hz); 5.80(d, 1H, J=8Hz).

(7R)-7-[2-(5-Amino-[1,2,4]thiadiazol-3-yl)-2-hydroxyimino-acetylamino]-8-oxo-3-([1,2,3]thiadiazol-5-ylsulfanyl)-5-thia-1-aza-bicyclo[4.2.0]oct-2-ene-2-carboxylic acid (39)

$^1$H NMR (D$_2$O) δ 3.30 (d, 1H, J=17 Hz); 3.74 (d, 1H, J=17 Hz); 5.22 (d, 1H, J=5 Hz); 5.80 (d, 1H, J=5 Hz); 8.58 (s, 1H).

(7R)-7-[2-(2-Amino-5-chlorothiazol-4-yl)-2-hydroxyimino-acetylamino]-8-oxo-3-(4H-[1,2,4]triazol-3-ylsulfanyl)-5-thia-1-aza-bicyclo[4.2.0]oct-2-ene-2-carboxylic acid (40)

$^1$H NMR (D$_2$O+NaHCO$_3$) δ 3.38 (d, 1H, J=17 Hz); 3.52 (d, 1H, J=17 Hz); 5.18 (d, 1H, J=5 Hz); 5.78 (d, 1H, J=5 Hz); 8.318 (s, 1H).

(7R)-7-[2-(2-Amino-5-chlorothiazol-4-yl)-2-trityloxyiminoacetylamino]-8-oxo-3-([1,3,4]thiadiazol-2-ylsulfanyl)-5-thia-1-aza-bicyclo[4.2.0]oct-2-ene-2-carboxylic acid benzhydryl ester A solution of [1,3,4]thiadiazole-2-thiol (56 mg, 0.46 mmol), 3-chloro cephem XIVb (360 mg g, 0.47 mmol) and tetrabutylammonium bromide (190 mg, 0.6 mmol) in dichloromethane (1.5 mL) was stirred vigorously with aqueous sodium bicarbonate (0.6 mL, 1.0 M). After 1 hr at room temperature the reaction mixture was partitioned between dichloromethane and water and the organic layer was dried over anhydrous sodium sulfate. After evaporating the solvent under reduced pressure the title compound (43 mg, 11%) was isolated by radial chromatography on silica gel (dichloromethane/methanol 200:1).

(7R)-7-[2-(2-Amino-5-chlorothiazol-4-yl)-2-hydroxyiminoacetylamino]-8-oxo-3-([1,3,4]thiadiazol-2-ylsulfanyl)-5-thia-1-aza-bicyclo[4.2.0]oct-2-ene-2-carboxylic acid (41)

To a solution of (7R)-7-[2-(2-Amino-5-chlorothiazol-4-yl)-2-trityloxyiminoacetylamino]-8-oxo-3-([1,3,4]thiadiazol-2-ylsulfanyl)-5-thia-1-aza-bicyclo[4.2.0]oct-2-ene-2-acid benzhydryl ester (43 mg, 0.05 mmol) in dichloromethane (2.2 mL) was added triethylsilane (0.45 mL). The mixture was cooled to 0° C. and trifluoroacetic acid (2.2 mL) was added. After 1 hr reaction at 0° C. the reaction mixture was concentrated under vacuum and diisopropyl ether was added to the oily residue. The title compound precipitated and was filtered, washed with additional diisopropyl ether and dried under vacuum (16 mg, 57%)

$^1$H NMR (D$_2$O+NaHCO$_3$) δ 3.38 (d, 1H, J=16 Hz); 3.80 (d, 1H, J=16 Hz); 5.20 (d, 1H, J=6 Hz); 5.82 (d, 1H, J=6 Hz); 9.30 (s, 1H).

(7R)-7-[2-[5-chloro-2-(tritylamino)-thiazol-4-yl]-2-(2-fluoro-ethoxyimino)-acetylamino]-3-(5-amino-[1,3,4]thiadiazol-2-ylsulfanyl)-8-oxo-5-thia-1-aza-bicyclo[4.2.0]oct-2-ene-2-carboxylic acid t-butyl ester A solution of (7R)-3-chloro-7-[2-[5-chloro-2-(tritylamino)-thiazol-4-yl]-2-(2-fluoroethoxyimino)-acetylamino]-8-oxo-5-thia-1-aza-bicyclo[4.2.0]oct-2-ene-2-carboxylic acid t-butyl ester XV (45 mg, 0.057 mmol) and sodium 5-amino-[1,3,4]thiadiazole-2-thiolate (10 mg, 0.064 mmol) in DMF (0.5 mL) was stirred at room temperature for 3 hr. The reaction mixture was partitioned between ethyl acetate and water. The organic layer was separated and dried over anhydrous sodium sulfate. After evaporating the solvent under reduced pressure the title compound (8 mg, 16%) was isolated by radial chromatography on silica gel (dichloromethane/methanol 50:1).

$^1$H NMR (CDCl$_3$/CD$_3$OD) δ 1.45 (s, 9H); 3.32 (d, 1H, J=16 Hz); 3.48 (d, 1H, J=16 Hz); 4.30–4.70 (m, 4H) 5.00 (d, 1H, J=6 Hz); 5.82 (d, 1H, J=6 Hz); 7.15–7.30 (m,16H).

(7R)-7-[2-(2-Amino-5-chlorothiazol-4-yl)-2-(2-fluoroethoxyimino)-acetylamino]-3-(5-amino-[1,3,4]thiadiazol-2-ylsulfanyl)-8-oxo-5-thia-1-aza-bicyclo[4.2.0]oct-2-ene-2-carboxylic acid (42)

To a solution of (7R)-7-[2-[5-chloro-2-(tritylamino)-thiazol-4-yl]-2-(2-fluoro-ethoxyimino)-acetylamino]-3-(5- amino-[1,3,4]thiadiazol-2-ylsulfanyl)-8-oxo-5-thia-1-aza-bicyclo[4.2.0]oct-2-ene-2-carboxylic acid t-butyl ester (8 mg, 0.009 mmol) in dichloromethane (0.16 mL) was added triethylsilane (0.04 mL), followed by trifluoroacetic acid (0.16 mL). After 3 hr at room temperature the reaction mixture was concentrated under vacuum and diisopropyl ether was added to the oily residue. The title compound precipitated and was filtered, washed with additional diisopropyl ether and dried under vacuum (3 mg, 32%).

$^1$H NMR ($D_2O/CD_3CN$) δ 3.82 (d, 1H, J=16 Hz); 4.03 (d, 1H, J=16 Hz); 4.70–5.20 (m, 4H); 5.40 (d, 1H, J=6 Hz); 6.22 (d, 1H, J=6 Hz).

(7R)-7-[2-(2-Amino-5-chlorothiazol-4-yl)-2-trityloxyimino-acetylamino]-8-oxo-3-([1,2,3]thiadiazol-5-ylsulfanyl)-5-thia-1-aza-bicyclo[4.2.0]oct-2-ene-2-carboxylic acid benzhydryl ester To a stirred solution of sodium 1,2,3-thiadiazole-5-thiolate dihydrate (264 mg, 1.50 mmol) in DMF (5 mL) was added at room temperature 3-chloro cephem XIVb (1.04 g, 1.23 mmol). The reaction mixture was stirred overnight and then was partitioned between ethyl acetate and water. The organic layer was dried over anhydrous sodium sulfate and the solvent removed under reduced pressure. The residue was chromatographed on silica gel column (ethyl acetate/hexane 1:2) to give the title compound (570 mg, 50%).

$^1$H NMR ($CDCl_3/CD_3OD$) δ 3.10 (d, 1H, J=16 Hz); 3.38 (d, 1H, J=16 Hz); 5.05 (d, 1H, J=6 Hz); 5.98 (d, 1H, J=6 Hz); 6.92 (s, 1H); 7.10–7.40 (m, 25H); 8.40 (s, 1H).

(7R)-7-[2-(2-Amino-5-chlorothiazol-4-yl)-2-hydroxyiminoacetylamino]-8-oxo-3-([1,2,3]thiadiazol-5-ylsulfanyl)-5-thia-1-aza-bicyclo[4.2.0]oct-2-ene-2-carboxylic acid (43)

To a solution of (7R)-7-[2-(2-amino-5-chlorothiazol-4-yl)-2-trityloxyiminoacetylamino]-8-oxo-3-([1,2,3]thiadiazol-5-ylsulfanyl)-5-thia-1-aza-bicyclo[4.2.0]oct-2-ene-2-carboxylic acid benzhydryl ester (570 mg, 0.61 mmol) in dichloromethane (5 mL) was added triethylsilane (2.5 mL) followed by addition of trifluoroacetic acid (5 mL). After 30 min at 0° C. the reaction mixture was concentrated under vacuum and diisopropyl ether was added to the oily residue. The title compound precipitated and was filtered, washed with diisopropyl ether and dried under vacuum (380 mg). The crude product was dissolved in water/1.0 M aqueous sodium bicarbonate. The solution was loaded onto an HP20 column and inorganics were removed by washing the column thoroughly with water. The title compound was isolated by eluting with 4:1 acetonitrile/water mixture, removing acetonitrile under reduced pressure and lyophilizing the residue (145 mg, 43%).

$^1$H NMR ($D_2O$) δ 3.30 (d, 1H, J=16 Hz); 3.72 (d, 1H, J=16 Hz); 5.20 (d, 1H, J=6 Hz); 5.81 (d, 1H, J=6 Hz); 8.58 (s, 1H).

(7R)-7-[2-(2-Amino-5-chlorothiazol-4-yl)-2-hydroxyiminoacetylamino]-3-(5-methylsulfanyl-[1,3,4]thiadiazol-2-ylsulfanyl)-8-oxo-5-thia-1-aza-bicyclo[4.2.0]oct-2-ene-2-carboxylic acid (44)

H NMR ($CD_3OD$) δ 2.74 (s, 3H); 3.40 (d, 1H, J=17 Hz); 3.83 (d, 1H, J=17 Hz); 5.20 (d, 1H, J=5 Hz); 5.88 (d, 1H, J=5 Hz).

(7R)-7-[2-(2-Amino-5-chlorothiazol-4-yl)-2-hydroxyiminoacetylamino]-3-(3-methyl-[1,2,4]oxadiazol-5-ylsulfanyl)-8-oxo-5-thia-1-aza-bicyclo[4.2.0]oct-2-ene-2-carboxylic acid (45)

$^1$H NMR ($D_2O$) δ 2.20 (s, 3H), 3.43 (d, 1H, J=17 Hz); 3.85 (d, 1H, J=17 Hz); 5.25 (d, 1H, J=5 Hz); 5.82 (d, 1H, J=5 Hz).

(7R)-7-[2-(2-Amino-5-chlorothiazol-4-yl)-2-hydroxyiminoacetylamino]-3-(3-amino-[1,2,4]thiadiazol-5-ylsulfanyl)-8-oxo-5-thia-1-aza-bicyclo[4.2.0]oct-2-ene-2-carboxylic acid (47)

$^1$H NMR ($CD_3OD$) δ 3.60 (d, 1H, J=17 Hz); 4.02 (d, 1H, J=17 Hz); 5.30 (d, 1H, J=5 Hz); 6.02 (d, 1H, J=5 Hz).

(7R)-7-[2-(2-Amino-5-chlorothiazol-4-yl)-2-hydroxyiminoacetylamino]-3-([1,3,4]oxadiazol-2-ylsulfanyl)-8-oxo-5-thia-1-aza-bicyclo[4.2.0]oct-2-ene-2-carboxylic acid (48)

$^1$H NMR ($D_2O$) δ 3.40 (d, 1H, J=17 Hz); 3.80 (d, 1H, J=17 Hz); 5.22 (d, 1H, J=5 Hz); 5.82 (d, 1H, J=5 Hz); 8.80 (s, 1H).

3-(5-Amino-[1,3,4]thiadiazol-2-ylsulfanyl)-(7R)-7-[2-(2-aminothiazol-4-yl)-2-hydroxyiminoacetylamino]-8-oxo-5-thia-1-aza-bicyclo[4.2.0]oct-2-ene-2-carboxylic acid (49)

$^1$H NMR ($D_2O$) δ 3.33 (d, 1H, J=16 Hz); 3.64 (d, 1H, J=16 Hz); 5.18 (d, 1H, J=5 Hz); 5.74 (d, 1H, J=5 Hz); 6.85 (s, 1H).

(7R)-7-[2-(5-Amino-[1,2,4]thiadiazol-3-yl)-2-hydroxyiminoacetylamino]-8-oxo-3-([1,3,4]thiadiazol-2-ylsulfanyl)-5-thia-1-aza-bicyclo [4.2.0]oct-2-ene-2-carboxylic acid (50)

$^1$H NMR ($D_2O$) δ 3.39 (d, 1H, J=16 Hz); 3.70 (d, 1H, J=16 Hz); 5.25 (d, 1H, J=6 Hz); 5.81 (d, 1H, J=6 Hz); 9.30 (s, 1H).

3-(5-Amino-[1,3,4]thiadiazol-2-ylsulfanyl)-(7R)-7-[2-(2-amino-thiazol-4-yl)-acetylamino]-8-oxo-5-thia-1-aza-bicyclo[4.2.0]oct-2-ene-2-carboxylic acid (51)

$^1$H NMR ($CD_3OD$) δ 3.33 (d, 1H, J=17 Hz); 3.44 (s, 2H); 3.58 (d, 1H, J=17 Hz); 5.00 (d, 1H, J=5 Hz); 5.47 (d, 1H, J=5 Hz); 6.40 (s, 1H).

(7R)-7-[2-(2-Amino-5-chlorothiazol-4-yl)-2-hydroxyiminoacetylamino]-3-(3-chloro-[1,2,4]thiadiazol-5-ylsulfanyl)-8-oxo-5-thia-1-aza-bicyclo [4.2.0]oct-2-ene-2-carboxylic acid (52)

$^1$H NMR ($D_2O$) δ 3.45 (d, 1H, J=17 Hz); 3.89 (d, 1H, J=17 Hz); 5.30 (d, 1H, J=5 Hz); 5.85 (d, 1H, J=5 Hz).

(7R)-7-[2-(2-Amino-5-chlorothiazol-4-yl)-2-hydroxyiminoacetylamino]-3-(5-amino-[1,3,4]thiadiazol-2-ylsulfanyl)-5,8-dioxo-5$\lambda^4$-thia-1-aza-bicyclo[4.2.0]oct-2-ene-2-carboxylic acid (53)

$^1$H NMR ($D_2O$) δ 3.52 (d, 1H, J=17 Hz); 3.89 (d, 1H, J=17 Hz); 4.80 (d, 1H, J=5 Hz); 5.80 (d, 1H, J=5 Hz).

(7R)-7-[2-(2-Amino-5-chlorothiazol-4-yl)-2-hydroxyiminoacetylamino]-3-(5-amino-[1,3,4]thiadiazol-2-ylsulfanyl)-8-oxo-5-thia-1-aza-bicyclo [4.2.0]oct-2-ene-2-carboxylic acid 2,2-dimethylpropionyloxymethyl ester (54)

To a stirring solution of (7R)-7-[2-(2-amino-5-chlorothiazol-4-yl)-2-hydroxyiminoacetylamino]-3-(5-amino-[1,3,4]thiadiazol-2-ylsulfanyl)-8-oxo-5-thia-1-aza-bicyclo[4.2.0]oct-2-ene-2-carboxylic acid, sodium salt (65 mg, 0.117 mmol) in DMF (0.3 mL) under nitrogen was added iodomethyl pivalate (31 mg, 0.128 mmol). After 1 h, water was added dropwise, and the precipitated product was removed by filtration to give 60.9 mg of the title compound.

$^1$H NMR (CDCl$_3$/CD$_3$OD) δ 3.39 (d, 1H, J=16), 4.44 (d, 1H, J=16), 4.99 (d, 1H, J=8), 5.78 (d, 1H, J=10), 5.80 (d, 1H, J=8), 5.85 (d, 1H, J=10)

(7R)-7-[2-(5-Amino-[1,2,4]thiadiazol-3-yl)-2-hydroxyiminoacetylamino]-3-(5-amino-[1,3,4]thiadiazol-2-ylsulfanyl)-8-oxo-5-thia-1-aza-bicyclo[4.2.0]oct-2-ene-2-carboxylic acid 2,2-dimethylpropionyloxymethyl ester (55)

$^1$H NMR (CD$_3$OD) δ 1.20(s, 9H); 3.42 (d, 1H, J=17 Hz); 3.68 (d, 1H, J=17 Hz); 5.24 (d, 1H, J=5 Hz); 5.98 (d, 1H, J=5 Hz); 5.24 (d, 1H, J=6 Hz); 5.86–5.98 (m, 3H).

BIOLOGICAL

Susceptibility Testing

Compounds were evaluated for antimicrobial activity against a panel of bacterial strains using a broth microdilution assay performed as recommended by the NCCLS (NCCLS (National Committee for Clinical Laboratory Standards). 1993. Methods for dilution antimicrobial susceptibility tests for bacteria that grow aerobically. NCCLS Document M7-A3, 1993. In: NCCLS Antimicrobial Susceptibility Testing, 3$^{rd}$ Ed.)

The minimum inhibitory concentration (MIC) is defined as the lowest concentration of a compound that prevents the growth of the bacteria.

Inoculum Preparation

Staphylococcus aureus strain Smith (ATCC 13709, penicillin-susceptible) or strain 76 (methicillin-resistant) was cultured overnight at 37° C. in brain-heart infusion broth (BHIB). The following morning, a portion of the culture was transferred to fresh BHIB and incubated for an additional 4–5 hours at 37° C. The cells were harvested by centrifugation, washed twice with PBS, and adjusted to the desired inoculum amount. The cell suspension was mixed with an equal volume of sterile 14% hog-gastric mucin (Comber K. R.; Osborne C. D.; Sutherland R.: Comparative effects of amoxicillin and ampicillin in the treatment of experimental mouse infections. *Antimicrobial Agents and Chemotherapy* 7(2):179–185, 1975). The inoculum was kept in an ice bath until used (preferably in less than one hour).

Experimental Infection

Male Swiss-Webster mice were challenged intraperitoneally with 0.5 mL of a bacterial suspension of *S. aureus* strain Smith (LD$_{50}$). Test compounds were administered subcutaneously in 0.1 mL volumes immediately after inoculation and 2 hours later. The animals were observed for 72 h. The total dose associated with 50% survival (ED$_{50}$) was determined using the probit method (Pasiello, A. P., J. M. Essigmann, and G. N. Wogan.: Rapid and accurate determination of median lethal dose (LD50) and its error with a small computer. *J Toxicol. Environ. Health*. 3:797–809, 1977).

Human Serum Binding

Binding of several representative compounds of this invention in pooled human serum was determined using ultrafiltration. Compounds were incubated in serum for 10 minutes at 37° C. in a shaking water bath. Serum ultrafiltrate was accomplished by centrifugation (Amicon Centrifree) for 20 minutes at 25° C. Compound content in the ultrafiltrate was quantified by HPLC. An ultrafilrate obtained by following the same procedure with no added compound was used as a standard.

An estimate of human serum binding (HSB*) was obtained for some compounds using the MIC values against *S. aureus* ATCC 29213 determined in growth medium (GM) and in a 1:1 mixture of growth medium and human serum (GM+HS):

$$HSB^* = (MIC_{GM+HS} - MIC_{GM})/MIC_{GM}\ 100\%$$

CONCLUSION

Those skilled in the art will readily appreciate that the present invention is well adapted to carry out the objectives and obtain the ends and advantages expressly described, as well as any that are inherent herein. The methods, procedures, treatments, molecules and specific compounds described herein representative presently preferred embodiments of this invention, are exemplary only and are not intended, nor are they to be construed, as limitations on the scope of the invention. Changes herein and other uses will occur to those skilled in the art based on the disclosures herein; such changes and uses are within the scope of this invention.

The patents and publications mentioned in the specification are indicative of the levels of skill in the art to which the invention pertains. All patents and publications are incorporated by reference to the same extent as if each individual publication was specifically and individually indicated to be incorporated by reference.

Other embodiments are within the following claims.

What is claimed:

1. A compound having the chemical formula

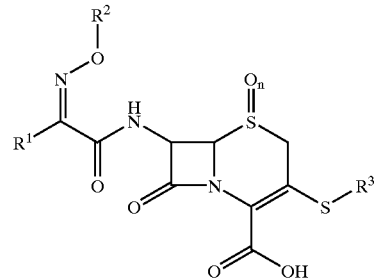

or a pharmaceutically acceptable salt thereof, wherein:

R$^1$ is selected from the group consisting of:

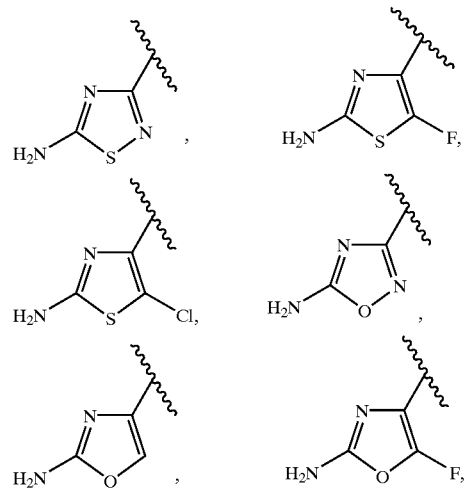

-continued

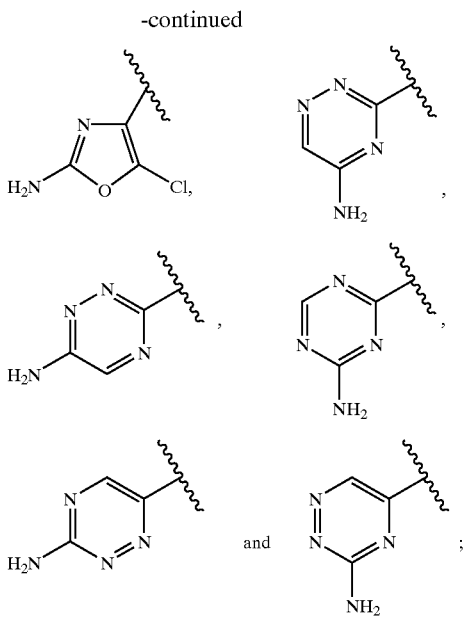

$R^3$ is selected from the group consisting of

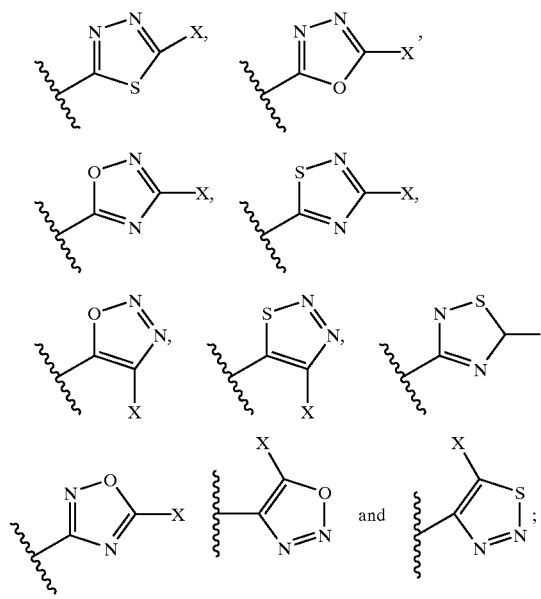

wherein X is selected from the group consisting of —NH$_2$, —NHSO$_2$NH$_2$ and —SO$_2$NH$_2$; and, n is 0 or 1.

2. The compound or salt of claim 1, wherein $R^1$ is selected from the group consisting of

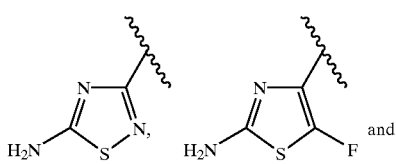

-continued

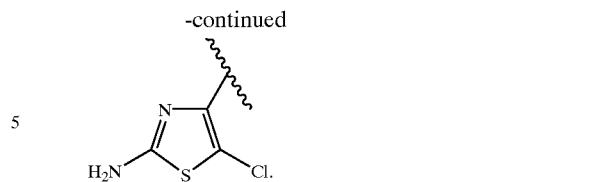

3. The compound or salt of claim 1, wherein $R^3$ is selected from the group consisting of:

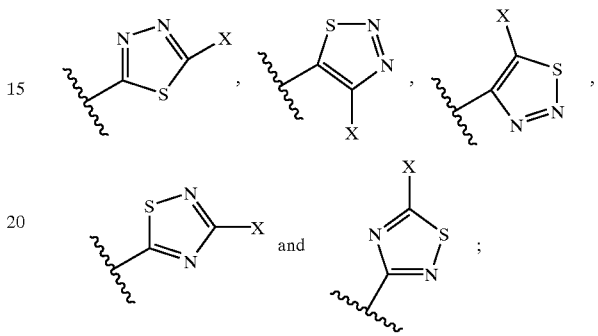

wherein X is selected from the group consisting of —NH$_2$, —NHSO$_2$NH$_2$ and —SO$_2$NH$_2$.

4. The compound or salt of claim 1, wherein $R^3$ is selected from the group consisting of:

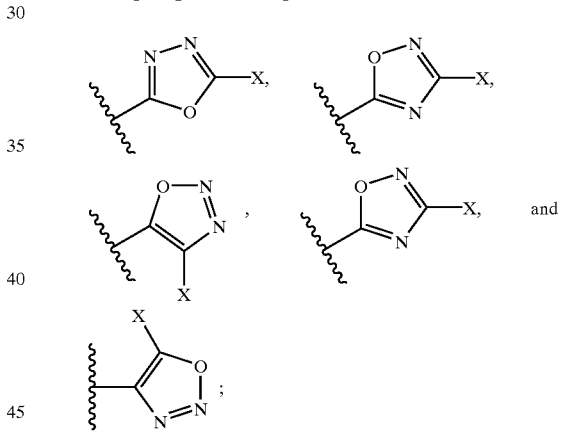

wherein X is selected from the group consisting of —NH$_2$, —NHSO$_2$NH$_2$ and —SO$_2$NH$_2$.

5. The compound or salt of either claim 3 or claim 4, wherein X is NH$_2$.

6. The compound of claim 1, wherein $R^1$ is selected from the group consisting of

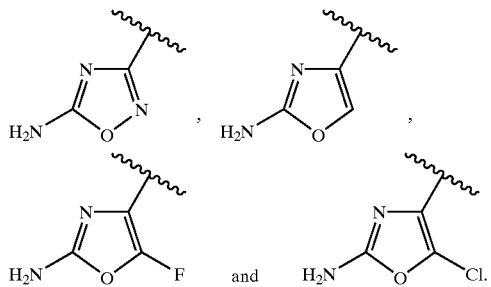

7. The compound of claim 1, wherein $R^1$ is selected from the group consisting of

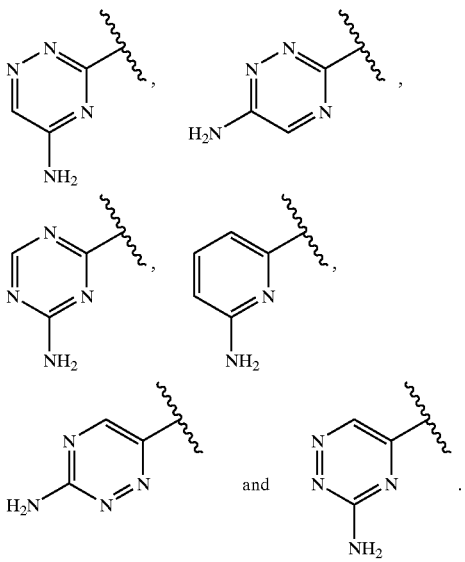

and

8. The compound or salt of claim 1, wherein:

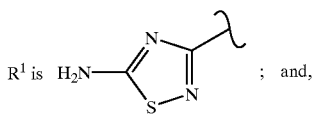

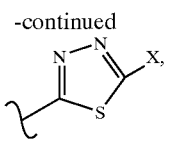

wherein n is 0 and X is —NH$_2$.

9. The compound or salt of claim 1, wherein:

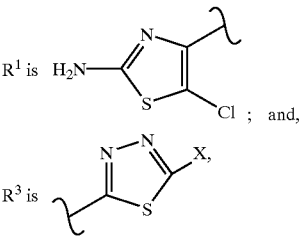

wherein n is 0 an X is —NH$_2$.

10. A method for treating a methicillin-resistant Staphylococcal infection, comprising administering to a patient in need thereof therapeutically effective amount of a compound or salt of any one of claims 1, 2, 3, 4, 7, 8 and 9.

11. The method of claim 10, wherein the Staphylococcal infection is caused by *S. aureus* Col (Meth$^R$)(bla−), *S. aureus* 76 (Meth$^R$)(bla+), *S. aureus* ATCC 33593 (Meth$^R$), *S. aureus* Spain #356 (Meth$^R$), and *S. haemolyticus* 05 (Meth$^R$).

12. An pharmaceutical composition, comprising:
a therapeutically effective amount of a compound or salt of any one of claims 1–9; and,
a pharmaceutically acceptable carrier.

* * * * *

UNITED STATES PATENT AND TRADEMARK OFFICE
CERTIFICATE OF CORRECTION

PATENT NO. : 6,599,893 B2
DATED : July 29, 2003
INVENTOR(S) : Tomasz W. Glinka

It is certified that error appears in the above-identified patent and that said Letters Patent is hereby corrected as shown below:

Column 44,
Lines 31-43, the chemical structure of the cephalosporin should be (i.e., $R^2$ should be replaced by a hydrogen atom).

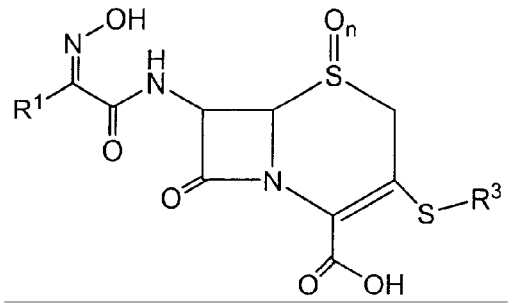

Signed and Sealed this

Tenth Day of August, 2004

JON W. DUDAS
*Acting Director of the United States Patent and Trademark Office*